US008652790B2

(12) United States Patent
Valentine et al.

(10) Patent No.: US 8,652,790 B2
(45) Date of Patent: Feb. 18, 2014

(54) CONFORMATIONAL ENTROPY IN MOLECULAR RECOGNITION

(75) Inventors: Kathleen G. Valentine, Ivyland, PA (US); Michael Marlow, Fort Lee, NJ (US); Andrew J. Wand, Philadelphia, PA (US); Kendra K. Frederick, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 773 days.

(21) Appl. No.: 12/669,626

(22) PCT Filed: Jul. 18, 2008

(86) PCT No.: PCT/US2008/070436

§ 371 (c)(1), (2), (4) Date: Jun. 22, 2010

(87) PCT Pub. No.: WO2009/012435

PCT Pub. Date: Jan. 22, 2009

(65) Prior Publication Data

US 2010/0285608 A1 Nov. 11, 2010

Related U.S. Application Data

(60) Provisional application No. 60/950,860, filed on Jul. 19, 2007.

(51) Int. Cl.
*G01N 31/00* (2006.01)
*G01N 33/53* (2006.01)

(52) U.S. Cl.
USPC ........... 435/7.21; 435/7.1; 436/501; 436/518; 530/300; 530/350; 424/130.1; 424/9.1; 422/430

(58) Field of Classification Search
None
See application file for complete search history.

(56) References Cited

U.S. PATENT DOCUMENTS

2006/0154323 A1 7/2006 Brown et al.

FOREIGN PATENT DOCUMENTS

WO WO 2009/012435 1/2009

OTHER PUBLICATIONS

Akke et al., "NMR order parameters and free-energy—an analytical approach and its application to cooperative Calcium (2+) binding by calbindin D9k", J. Am. Chem. Soc., Oct. 1993, 115(21), 9832-9833.
Aoyagi et al., "Structural basis for endothelial nitric oxide synthase binding to calmodulin", The EMBO Journal, Feb. 17, 2003, 22(4), 766-775.
Best et al., "The origin of protein sidechain order parameter distributions", J. Am. Chem. Soc., Jun. 30, 2004, 126(25), 7734-7735.
Best et al., "What contributions to protein side-chain dynamics are probed by NMR experiments? A molecular dynamics simulation analysis", J. Mol. Biol., May 27, 2005, 349(1), 185-203.
Brokx et al., "Energetics of target peptide binding by calmodulin reveals different modes of binding", J. Biol. Chem., Apr. 27, 2001, 276(17), 14083-14091.
Chou et al., "Insights into the mobility of methyl-bearing side chains in proteins from $^3J_{cc}$ and $^3J_{CN}$ couplings", J. Am. Chem. Soc., Jun. 2003, 125(29), 8959-8966.
Clackson et al., "A hot spot of binding energy in a hormone-receptor interface", Science, Jan. 20, 1995, 267(5196), 383-386.
Clapperton et al., "Structure of the complex of calmodulin with the target sequence of calmodulin-dependent protein kinase I: studies of the kinase activation mechanism", Biochemistry, Dec. 17, 2002, 41(50), 14669-14679.
Cooper et al., "Allostery without conformational change—a plausible model", Eur. Biophys. J. Biophys. Lett., Oct. 1984, 11(2), 103-109.
Dellwo et al., "Model-independent and model-dependent analysis of the global and internal dynamics of cyclosporine A", J. Am. Chem. Soc., Jun. 1989, 3(13), 4571-4578.
Farrow et al., "Backbone Dynamics of a Free and Phosphopeptide-Complexed Src Homology 2 Domain Studied by 15N NMR Relaxation", Biochemistry, May 17, 1994, 33(19), 5984-6003.
Frederick et al., "Conformational Entropy in Molecular Recognition by Protein", Nature, Jul. 19, 2007, 448(7151), 325-329.
Gaboriaud et al., "Hydrophobic cluster analysis: an efficient new way to compare and analyse amino acid sequences", FEBS letters, Nov. 16, 1987, 224(1), 149-155.
Gebel, "Proteins 'Jiggle' May Give a Jolt", The Philadelphia Inquirer, Jul. 19, 2007, 3 pages.
AccessionNo._AAD45181.1_Jul. 21, 1999.
Goldberg et al., "Structural basis for the autoinhibition of calcium/calmodulin-dependent protein kinase I", Cell, Mar. 22, 1996, 84(6), 875-887.
Grunberg et al., "Flexibility and conformational entropy in protein-protein binding", Structure, Apr. 1, 2006, 14(4), 683-693.
Hilser et al., "A statistical thermodynamic model of the protein ensemble", Chem. Rev., May 2005, 106(5), 1545-1558.
Igumenova et al., "Characterization of the fast dynamics of protein amino acid side chains using NMR relaxation in solution", Chem. Rev., May 2006, 106(5), 672-1699.
Kahl et al., "Regulation of cell cycle progression by calcium/calmodulin-dependent pathways", Endocr. Rev., Dec. 2003, 24(6), 719-736.
Kainosho et al., "Optimal isotope labelling for NMR protein structure determinations", Nature, Mar. 2, 2006, 440(7080), 52-57.
Karplus et al., "Configurational entropy of native proteins", Biophys. J., Dec. 1987, 52(6), 1083-1085.
Kranz et al., "A direct test of the reductionist approach to structural studies of calmodulin activity: relevance of peptide models of target proteins", J. Biol. Chem., May 10, 2002, 277(19), 16351-16354.

(Continued)

*Primary Examiner* — Lisa Cook
(74) *Attorney, Agent, or Firm* — Baker & Hostetler LLP

(57) ABSTRACT

The present invention provides methods for the determination of the degree of molecular recognition of a protein with a ligand, including a first protein with a second protein. The methods may comprise determining the squared generalized order parameter (hereinafter, O) for at least one intramolecular bond of the first protein. The protein is then formed into a complex with a ligand. The value or values of O2 for the said at least one bond of the protein is then determined while the protein and the ligand are in the complex. The O value or values determined for the protein while the protein and the ligand are in a complex are compared or related to the O value or values determined for the uncomplexed protein.

16 Claims, 5 Drawing Sheets

(56) References Cited

OTHER PUBLICATIONS

Kranz et al., "Dissection of the pathway of molecular recognition by calmodulin", Biochemistry, Feb. 26, 2002, 41(8), 2599-2608.
Lee et al., "Microscopic origins of entropy, heat capacity and the glass transition in proteins", Nature, May 24, 2001, 411(19), 501-504.
Lee et al., "Redistribution and loss of side chain entropy upon formation of a calmodulin-peptide complex", Nature Struct. Biol., Jan. 2000, 7(1), 72-77.
Lee et al., "Temperature dependence of the internal dynamics of a calmodulin-peptide complex", Biochemistry, Nov. 19, 2002, 41(46), 13814-13825.
Li et al., "Insights into the local residual entropy of proteins provided by NMR relaxation", Prot. Sci., Dec. 1996, 5(12), 2647-2650.
Lipari et al., "Model-free approach to the interpretation of nuclear magnetic-resonance relaxation in macromolecules. 1. Theory and range of validity", J. Am. Chem. Soc., Aug. 1982, 104(17), 4546-4559.
Lukas et al., "Calmodulin binding domains: characterization of a phosphorylation and calmodulin binding site from myosin light chain kinase", Biochemistry, Mar. 25, 1986, 25(6), 1458-1464.
Marcus, "Ionic volumes in solution", Biophysical chemistry, Dec. 1, 2006, 124(3), 200-207.
Marlow et al., "Conformational dynamics of calmodulin in complex with the calmodulin-dependent kinase kinase alpha calmodulin-binding domain", Biochemistry, Jul. 25, 2006, 45(29), 8732-8741.
Meador et al., "Target enzyme recognition by calmodulin: 2.4 A structure of a calmodulin-peptide complex", Science, Aug. 28, 1992, 257(5074), 1251-1255.
Muhandiram et al., "Measurement of 2H T1 and T1.rho. Relaxation Times in Uniformly 13C-Labeled and Fractionally 2H-Labeled Proteins in Solution", J. Am. Chem. Soc., Nov. 1995, 117(46), 11536-11544.
Osawa et al., "A novel target recognition revealed by calmodulin in complex with $Ca^{2+}$-calmodulin-dependent kinase kinase", Nat. Struct. Biol., Sep. 1999, 6(9), 819-824.
Scott, "On optimal and data-based histograms", Biometrika, Dec. 1979, 66(3), 605-610.
Song et al., "Temperature dependence of fast dynamics in proteins", Biophys. J., Mar. 15, 2007, 92(6), L43-L45.
Spolar et al., "Coupling of local folding to site-specific binding of proteins to DNA", Science Feb. 11, 1994, 263(5148), 777-784.
Steinberg, et al., "Entropy changes accompanying association reactions of proteins", J. Biol. Chem., Jan. 1963, 238(1), 172-181.
Sturtevant, "Heat capacity and entropy changes in processes involving proteins", Proc. Natl Acad. Sci. USA, Jun. 1, 1977, 74(6), 2236-2240.
Tokumitsu et al., "Calcium/calmodulin-dependent protein kinase kinase: identification of regulatory domains", Biochemistry, Oct. 21, 1997, 36(42), 12823-12827.
Ulrich et al., "BioMagResBank", Nucleic Acids Research, Jan. 2008, 36, D402-D408.
Wang et al., "Temperature dependence of anisotropic protein backbone dynamics", J. Am. Chem. Soc., Jun. 16, 2003, 125(28), 8639-8643.
Wang et al., "The role of backbone motions in ligand binding to the c-Src SH3 domain", Mol. Biol., Nov. 2, 2001, 313(4), 873-887.
Wintrode et al., "Energetics of target peptide recognition by calmodulin: a calorimetric study", J. Mol. Biol., Mar. 14, 1997, 266(5), 1050-1062.
Wodak et al., "Structural basis of macromolecular recognition", Adv. Prot. Chem., 2002, 61, 9-73.
Yap et al., "Calmodulin target database", J. Struct. Funct. Genom., Mar. 2000, 1(1), 8-14.
Zhang et al., "Characterization of the calmodulin-binding domain of rat cerebellar nitric oxide synthase", J. Biol. Chem., Jan. 14, 1994, 269(2), 981-985.

CONFORMATIONAL ENTROPY IN MOLECULAR RECOGNITION

CROSS-REFERENCE TO RELATED APPLICATIONS

This application is the National Stage of International Application No. PCT/US2008/070436, filed Jul. 18, 2008, which claims the benefit of U.S. Provisional Application No. 60/950,860, filed Jul. 19, 2007, the disclosures of which are incorporated herein by reference in their entireties.

GOVERNMENT RIGHTS

The United States Government may have rights in the invention described herein, which was made in part with funding from the National Institutes of Health, Grant No. DK 39806, A. J. Wand (PI).

SEQUENCE LISTING

The instant application contains a Sequence Listing which has been submitted in ASCII format via EFS-Web and is hereby incorporated by reference in its entirety. Said ASCII copy, created on Mar. 19, 2013, is named Sequence_Listing_CRF_UPN5472_U4566 and is 2,681 bytes in size.

FIELD OF THE INVENTION

The present invention pertains, among other things, to the characterization of the thermodynamics of molecule-molecule interactions, including protein-protein interactions.

BACKGROUND OF THE INVENTION

Molecular recognition by proteins is fundamental to almost every biological process, particularly the protein associations underlying cellular signal transduction. Understanding the basis for protein-protein interactions requires the full characterization of the thermodynamics of their association. Historically it has been virtually impossible to experimentally estimate changes in protein conformational entropy, a potentially important component of the free energy of protein association.

Numerous structural studies have revealed that protein-protein interfaces often involve dozens of amino acid residues and thousands of $Å^2$ of contact area. Wodak, S. J. & Janin, *J. Structural basis of macromolecular recognition. Adv. Prot. Chem.* 61, 9-73 (2002). It has also become apparent that a non-uniform contribution of individual residues to the free energy of binding can exist and that static structural analyses can mask important factors underlying the high-affinity interactions between proteins. Clackson, T. & Wells, J. A. *A hot spot of binding energy in a hormone-receptor interface. Science* 267, 383-386 (1995). Of particular interest is the role of protein conformational entropy in modulating the free energy of the association of a protein with a ligand. A simplistic decomposition emphasizes the fact that the entropy of binding ($\Delta S_{bind}$), obtainable by calorimetric methods, is comprised of contributions associated with the protein, the ligand and the solvent:

$$\Delta G_{bind} = \Delta H_{bind} - T\Delta S_{bind} = \Delta H_{bind} T(\Delta S_{protein} + \Delta S_{ligand} + \Delta S_{solvent}) \quad (1)$$

It is well established that the transitions of a ligand from a disordered (high entropy) unbound state to a structured (lower entropy) bound state can profoundly influence the entropy of macromolecular associations. Spolar, R. S. & Record, M. T. *Coupling of local folding to site-specific binding of proteins to DNA. Science* 263, 777-784. It is also well established that burial of hydrophobic surface area and the consequent release of hydration waters to the bulk solvent can also contribute significantly to the thermodynamics of binding. Sturtevant, J. M. *Heat capacity and entropy changes in processes involving proteins. Proc. Natl Acad. Sci. USA* 74, 2236-2240 (1977). What is less understood is the potential entropic contributions from a 'structured' protein ($\Delta S_{protein}$), 5 which includes changes in its conformational entropy ($\Delta S_{conf}$) as well as changes in rotational and translational entropy. Steinberg, I. Z. & Scheraga, H. A. *Entropy changes accompanying association reactions of proteins. J. Biol. Chem.* 238, 172-181 (1963); Cooper, A. & Dryden, D. T. F. *Allostery without conformational change—a plausible model. Eur. Biophys. J. Biophys. Lett.* 11, 103-109 (1984); Karplus, M., Ichiye, T & Pettitt, B. M. *Configurational entropy of native proteins. Biophys. J.* 52, 1083-1085 (1987).

SUMMARY OF THE INVENTION

Provided are, among other things, methods for the determination of the degree of molecular recognition of a protein for a ligand comprising: determining the squared generalized order parameter ($O^2$) for at least one intramolecular bond of the protein; forming a complex between the protein and the ligand; determining $O^2$ for the said at least one bond of the protein while the protein and the ligand are in a complex; and relating the $O^2$ value or values determined for the protein while the protein and the ligand are in a complex to the $O^2$ value or values determined for the uncomplexed protein.

DETAILED DESCRIPTION OF ILLUSTRATIVE EMBODIMENTS

Figure 1:
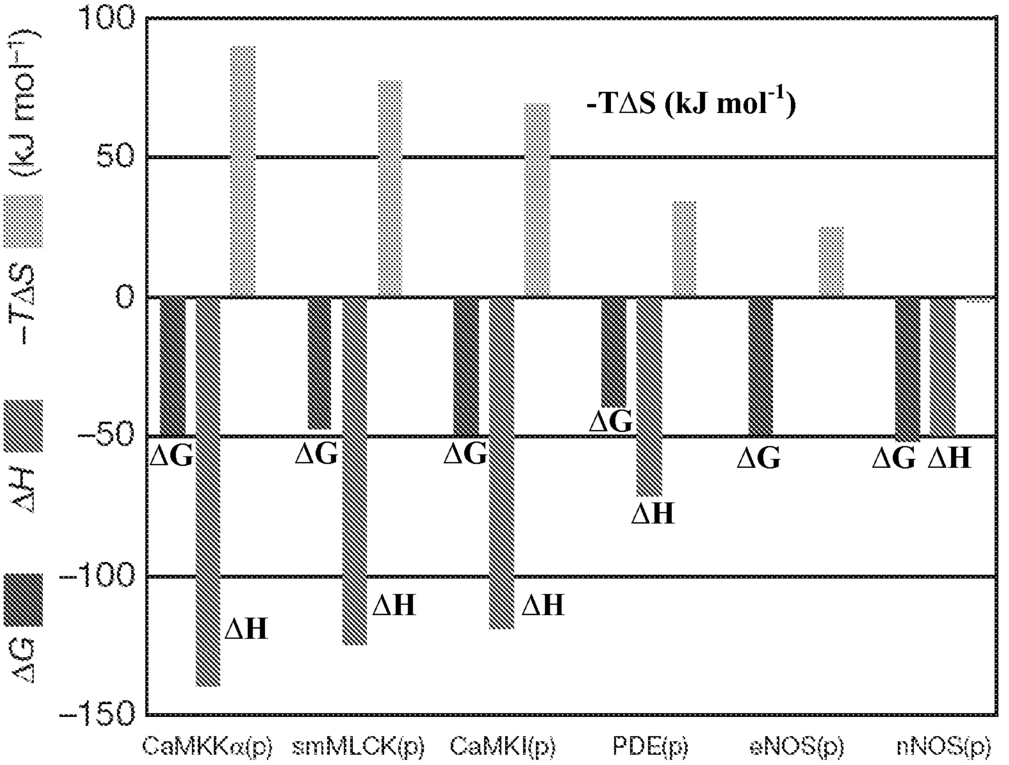
FIG. 1 illustrates the thermodynamic origins of high-affinity binding of target domains by calmodulin.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment.

The disclosures of each patent, patent application, and publication cited or described in this document are hereby incorporated herein by reference, in their entirety.

The present invention provides, inter alia, methods for the determination of the degree of molecular recognition of a protein with a ligand. The methods comprise determining the squared generalized order parameter (hereinafter, $O^2$) for at least one intramolecular bond of the protein. The protein is then formed into a complex with a ligand. The value or values of $O^2$ for the said at least one bond of the protein is then determined while the protein and ligand are in the complex. The $O^2$ value or values determined for the protein while the protein and ligand are in a complex are compared or related to the $O^2$ value or values determined for the uncomplexed protein.

It is now believed that the $O^2$ values are strongly related to conformational entropy of the proteins, or to their change upon complexation. Naturally, the proteins selected need to interact in some way in order to perceive different values. The techniques of this invention may be, and preferably are, performed on pluralities of proteins placed into complex or association with a first protein and, thereby, robust information on the strength or weakness of the protein-protein interactions may be obtained. Tables of intermolecular complexation data may easily be obtained, from which proteinaceous and small molecule lead drug candidates may be identified.

The determination of $O^2$ values is preferably obtained through employment of NMR analysis. In accordance with some embodiments of the invention, at least some of the bonds analyzed are treated as simple harmonic oscillators.

It is preferred to perform the processes of the invention iteratively, by complexing several or many proteins with the first protein to generate a data collection or table of interaction values. From this collection or table, relative strengths of molecular interactions may be ascertained. Accessing this data is a powerful research tool which, inter alia, facilitates identification of important interactions for design of drug candidates.

As provided above, while it is well established that burial of hydrophobic surface area and the consequent release of hydration waters to the bulk solvent also contribute significantly to the thermodynamics of binding, what is less understood is the potential entropic contributions from a 'structured' protein ($\Delta S_{protein}$), which includes changes in its conformational entropy ($\Delta S_{conf}$) as well as changes in rotational and translational entropy The present study elaborates on $\Delta S_{conf}$. As may be observed from equation (1), supra, the measurement of total system thermodynamic parameters does not resolve contributions from internal protein conformational entropy. The estimation of changes in conformational entropy due to protein-ligand (e.g., protein-protein) association from molecular dynamics simulations remains a considerable challenge. Grunberg, R., Nilges, M & Leckner, J. *Flexibility and conformational entropy in protein-protein binding. Structure* 14, 683-693 (2006). Experimental measurement of the conformational entropy of the protein in its free and complexed states is therefore required. It has been discovered that recent developments in nuclear magnetic resonance (NMR) relaxation methods and analysis now make this feasible.

The conformational entropy of proteins is manifested as motion between different structural states. Karplus, M., Ichiye, T. & Pettitt, B. M. *Configurational entropy of native proteins. Biophys. J.* 52, 1083-1085 (1987). It has been discovered that motion may be used as a proxy for conformational disorder or entropy. In principle, the measurement of a protein's internal dynamics should facilitate characterization of conformational entropy through a 'counting of states' implicit in molecular motio. Igumenova, T. I., Frederick, K. K. & Wand, A. J. *Characterization of the fast dynamics of protein amino acid side chains using NMR relaxation in solution. Chem. Rev.* 106, 1672-1699 (2006). Solution NMR spectroscopy is particularly well suited to measuring conformational dynamics over a wide-range of time scales. Cavanagh, J. et al. *Protein NMR spectroscopy: Principles and practice* 2*nd edn* (Elsevier, Burlington, Mass., 2006). Considerations lead to the conclusion that the motion expressed on the sub-nanosecond timescale corresponds to significant conformational entropy. Karplus, M, et al. (1987); Igumenova, T. I., et al. (2006). This timescale is directly accessed using NMR relaxation methods. Igumenova, T. I., et al. (2006).

Calmodulin as a Model System

Here calmodulin is employed as a model system to investigate the role for changes in protein conformational entropy in the high-affinity association of proteins. Calmodulin is a central participant in the calcium-mediated signal transduction pathways of eukaryotes. Kahl, C. R. & Means, A. R. *Regulation of cell cycle progression by calcium/calmodulin-dependent pathways. Endocr. Rev.* 24, 719-736 (2003). It interacts with and regulates the activity of approximately three-hundred proteins. Yap, K. L. et al. *Calmodulin target database. J. Struct. Funct. Genom.* 1, 8-14 (2000). Previously, using NMR relaxation methods, we have shown that calcium-saturated calmodulin (CaM) is an unusually dynamic protein and is characterized by a broad, non-uniform multi-modal distribution of the amplitude of fast side-chain dynamics. Lee, A. L., Kinnear, S. A. & Wand, A. J. *Redistribution and loss of side chain entropy upon formation of a calmodulin peptide complex. Nature Struct. Biol.* 7, 72-77 (2000). Binding of a target domain to CaM causes a significant redistribution of the fast side-chain dynamics in calmodulin. Id. This raises the possibility that CaM employs its internal conformational entropy to 'tune' its affinity for ligands.

NMR methods are herein used to determine the dynamic response of human CaM (GenBank AAD45181) to the binding of six peptides representing the calmodulin-binding domains of the smooth muscle myosin light chain kinase (smMLCK; AAA69964) (Lukas, T. J. et al. *Calmodulin binding domains: characterization of a phosphorylation and calmodulin binding site from myosin light chain kinase. Biochemistry* 25, 1458-1464 (1986)), the neuronal and endothelial nitric oxide synthases (nNOS and eNOS; AAB60654 and AAH63294, respectively) (Zhang, M. & Vogel, H. J. *Characterization of the calmodulin-binding domain of rat cerebellar nitric oxide synthase. J. Biol. Chem.* 269, 981-985 (1994)), the calmodulin kinase kinase (CaMKKα; EDM05132) (Tokumitsu, H. et al. *Calcium/calmodulin-dependent protein kinase kinase: identification of regulatory domains. Biochemistry* 36, 12823-12827 (1997)), the calmodulin kinase I (CaMKI; EAW63990) Goldberg, J., Nairn, A. C. & Kuriyan, *J. Structural basis for the autoinhibition of calcium/calmodulin-dependent protein kinase I. Cell* 84, 875-887 (1996)) and the phosphodiesterase (PDE; AAD40738 (SEQ ID NO: 8)) Goldberg, J., Nairn, A. C. & Kuriyan, *J. Structural basis for the autoinhibition of calcium/calmodulin-dependent protein kinase I. Cell* 84, 875-887 (1996)). Here the nomenclature smMLCK(p) is used to emphasize the fact that the present study employs peptide models of the calmodulin-binding domains of the regulated proteins. All of the calmodulin-binding domain peptides have a basic amphiphillic character and form α-helical structure when bound to calmodulin, as shown in Table 1, below.

TABLE 1

| Calmodulin Bindin Domains[a] | |
|---|---|
| nNOS(p) | KRRAIGFKKLAEAVKFSAKLMGQ (SEQ ID NO: 1) |
| eNOS(p) | RKKTFKEVANAVKISASLMG (SEQ ID NO: 2) |
| PDE(p) | QTEKMWQRLKGILRSLVKQ (SEQ ID NO: 3) |
| CaMKI(p) | AKSKWKQAFNATAVVRHMRKLQ (SEQ ID NO: 4) |
| smMLCK(p) | ARRKWQKTGHAVRAIGRLSS (SEQ ID NO: 5) |
| CaMKKα(p) | (COOH-FPNGFSRKRLMSKVLIVTTWSPLL (SEQ ID NO: 6) |

[a]Sequences of the six calmodulin-binding peptides. Note that CaMKKα(p) binds in opposite orientation to CaM relative to the other five peptides. For PDE(p), a C15S mutation has been used to avoid complications with oxidation.

Four of the peptides have been found previously by isothermal titration calorimetry to have roughly the same affinity for calmodulin but with widely different thermodynamic parameters defining the free energy of association. Wintrode, P. L. & Privalov, P. L. *Energetics of target peptide recognition by calmodulin: a calorimetric study. J. Mol. Biol.* 266, 1050-1062 (1997); Brokx, R. D. et al. *Energetics of target peptide binding by calmodulin reveals different modes of binding. J. Biol. Chem.* 276, 14083-14091 (2001). The present study repeats isothermal titration calorimetry measurements at a temperature (35° C.) that is more optimal for solution NMR spectroscopy, and characterizes the thermodynamics of binding of two additional domains (FIG. 1). Shown in FIG. 1 are the Gibbs free energy (ΔG), enthalpy (ΔH) and entropy (−TΔS) for the formation of the six calcium-saturated CaM-peptide complexes at 35° C., as determined by isothermal titration calorimetry. Values are tabulated in Table 2, below.

TABLE 2

Thermodynamics of Calmodulin Bindin of Target Domains[a]

| Domain | $\Delta G_{binding}^{total}$ (kJ/mol) | $\Delta H_{binding}^{total}$ (kJ/mol) | $-T\Delta S_{binding}^{total}$ (kJ/mol) |
|---|---|---|---|
| CaMKK(p)[b] | −49.8 ± 0.5 | −140.0 ± 0.9 | +90.0 ± 1.0 |
| smMLCK(p)[c] | −46.6 ± 0.1 | −124.7 ± 0.2 | +78.0 ± 0.3 |
| CaMK1p[c] | −49.5 ± 0.5 | −119.0 ± 0.4 | +69.6 ± 0.9 |

TABLE 2-continued

Thermodynamics of Calmodulin Bindin of Target Domains[a]

| Domain | $\Delta G_{binding}^{total}$ (kJ/mol) | $\Delta H_{binding}^{total}$ (kJ/mol) | $-T\Delta S_{binding}^{total}$ (kJ/mol) |
|---|---|---|---|
| PDE(p) | −37.9 ± 0.3 | −71.8 ± 0.6 | +33.9 ± 0.7 |
| eNOS(p) | −49.2 ± 0.3 | −74.9 ± 0.4 | +25.7 ± 0.8 |
| nNOS(p) | −51.7 ± 0.6 | −49.9 ± 0.3 | −1.9 ± 0.7 |

[a]Determined by isothermal titration calorimetry using calcium saturated calmodulin as titrant (200 μM) into 5-20 μM solutions of peptide. Solutions prepared in 20 mM imidazole (pH 6.5), 100 mM KCl, 6 mM $CaCl_2$ and 0.02% (w/v) $NaN_3$. Standard errors given. Data obtained at 308 K.

[b]From Marlow & Wand[1]

[c]From Frederick et al.[2]

In the case of the CaMKKα(p) and smMLCK(p) domains, binding is driven by a large favourable change in total binding enthalpy overcoming a large unfavourable change in total binding entropy. At the other extreme, nNOS(p) binding is driven by a favourable change in total enthalpy accompanied by a small favourable change in entropy. The PDE(p), CaMKI (p) and eNOS(p) calmodulin-binding domains represent intermediate cases. The entropy of binding of these domains varies by 90 kJ $mol^{-1}$ and changes sign (FIG. 1).

Titration of CaM with each of the peptides reveals that all six of the resulting complexes have a 1:1 stoichiometry and are in slow exchange with their dissociated components on the NMR $^1$H chemical shift timescale (not shown). The CaM-smMLCK(p), CaM-PDE(p) and CaM-CaMKKα(p) complexes have very little conformational heterogeneity, as judged by $^{15}$N- and $^{13}$C-heteronuclear single quantum correlation (HSQC) spectra, whereas the CaM-nNOS(p), CaM-eNOS(p) and CaM-CaMKI(p) complexes show some heterogeneity at a small number of locations in the calmodulin molecule. This was found to largely arise from populations of minor rotameric orientations of methyl-bearing side chains. These results indicate a range of localized conformational heterogeneity in calmodulin across the six calmodulin complexes. This heterogeneity represents classical conformational entropy.

The Dynamic Response of Calmodulin

The sub-nanosecond (sub-ns) dynamics of the polypeptide backbone of calmodulin in the six complexes were probed using NMR relaxation techniques. The degree of spatial restriction of each motional probe was assigned a number between 0, corresponding to complete isotropic disorder, and 1, corresponding to a fixed orientation in the molecular frame. This parameter is the squared generalized order parameter ($O^2$) as it applies to the amide N—H bond ($O^2_{NH}$), the $C_\alpha$—C' bond ($O^2_{c\alpha cO}$) and the methyl symmetry axis ($O^2_{axis}$). $O^2_{NH}$ parameters at amide nitrogen sites were obtained from measurements of $^{15}$N dipolar relaxation. Farrow, N. A. et al. *Backbone dynamics of a free and a phosphopeptide-complexed Src homology-2 domain studied by $^{15}$N NMR relaxation. Biochemistry* 33, 5984-6003 (1994). $O^2_{c\alpha cO}$ parameters were obtained from measurement of transverse cross-correlated relaxation between $^{13}$CO chemical shift anisotropy and the $^{13}$CO—$^{13}$Cα dipolar interactions. Wang, T., Cai, S. & Zuiderweg, E. R. *Temperature dependence of anisotropic protein backbone dynamics. J. Am. Chem. Soc.* 125, 8639-8643 (2003). The motion of methyl groups ($O^2_{axis}$) of calmodulin side chains were characterized using $^2$H spin relaxation methods. Muhandiram, D. R. et al. *Measurement of H-2 T-1 and T-1p relaxation-times in uniformly C-13-Labeled and fractionally H-2-labeled proteins in solution. J. Am. Chem. Soc.* 117, 11536-11544 (1995).

The dynamics of the backbone of calmodulin are invariant across the complexes, as indicated by the average $O^2_{NH}$ and $O^2_{C\alpha CO}$ parameters. Table 3, below, provides a summary of the backbone dynamics observed in the six calmodulin-target complexes.

TABLE 3[a]

| | $-T\Delta S_{bind}$ (kJ/mol) | $<O^2_{C\alpha CO}>$ | $<O^2_{NH}>$ |
|---|---|---|---|
| CaMKKα(p) | +90.0 ± 1.0 | 0.79 ± 0.21 | 0.93 ± 0.08 |
| smMLCK(p) | +78.0 ± 0.3 | 0.83 ± 0.12 | 0.92 ± 0.09 |
| CaMK1p | +69.6 ± 0.9 | 0.88 ± 0.14 | 0.94 ± 0.08 |
| PDE(p) | +33.9 ± 0.7 | n.d. | 0.92 ± 0.06 |
| eNOS(p) | +25.7 ± 0.8 | 0.86 ± 0.19 | 0.92 ± 0.09 |
| nNOS(p) | −1.9 ± 0.7 | 0.85 ± 0.16 | 0.92 ± 0.08 |

[a]Binding entropy at 308 K. Average values with standard deviations of the generalized order parameters of the CO—Cα ($<O^2_{C\alpha CO}>$) and N—H ($<O^2_{NH}>$) bond vectors of calmodulin in complex with the six target domains. Linear regression of $<O^2_{NH}>$ and ($<O^2_{C\alpha CO}>$) versus $-T\Delta S$ gives slopes of $9 \times 10^{-5}$ and $-4 \times 10^{-4}$ $kJ^{-1}$ and corresponding $R^2$ values of 0.27 and 0.21, respectively.

In contrast, the motion of methyl-bearing amino acid side chains varies significantly with the nature of the target domain. There are 56 methyl-bearing amino acids providing 80 methyl groups as probes distributed across the primary sequence of calmodulin and including nine methionines that line the target domain binding sites formed in the various complexes.

Dynamics as a Proxy for Entropy

Figure 4:
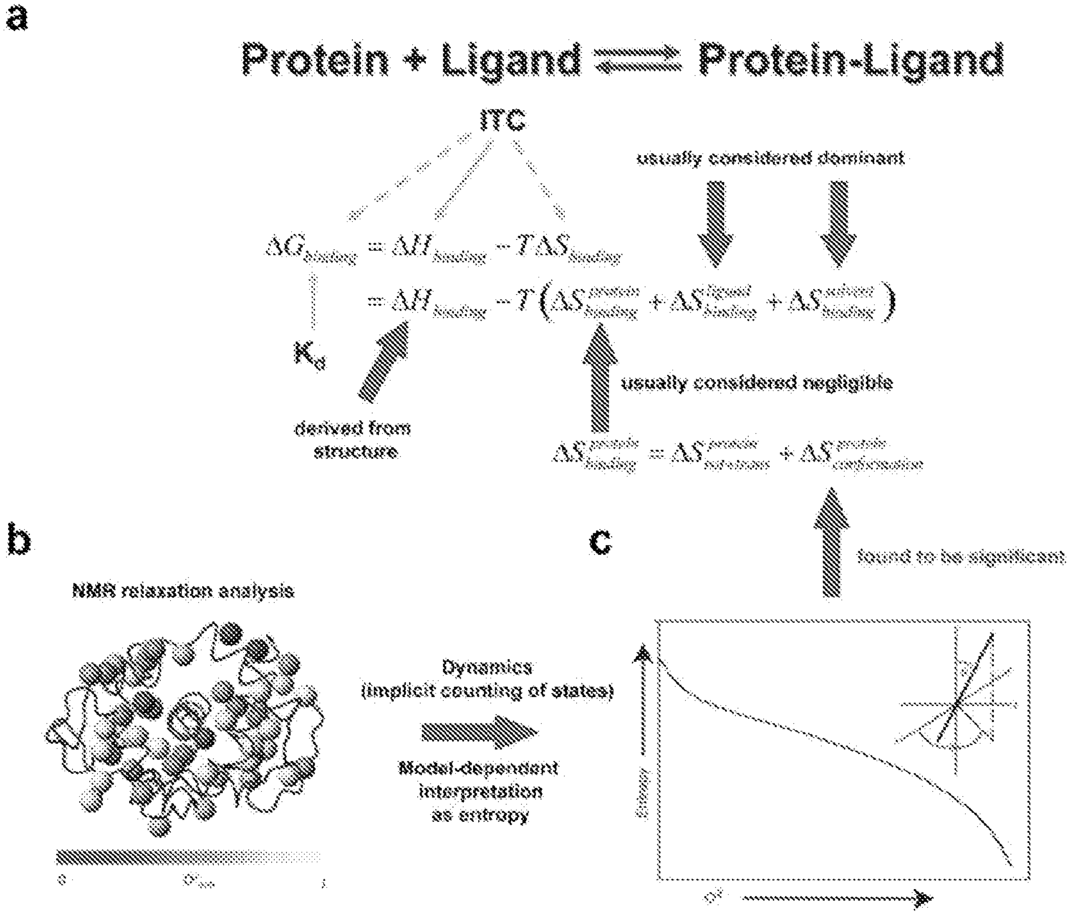
FIG. 4 provides an outline of the approach used to investigate the contribution of changes in the conformational entropy of calmodulin to the free energy of binding of target domains.

Guided by Karplus and co-workers (see Karplus M et al. (1987)), the present approach connects the change in internal protein dynamics to the conformational entropy, describing the protein as a disjoint multidimensional harmonic well:

$$S_{conf}=\Sigma p_i S^h_i - k_B \Sigma p_i lnp_i \qquad (2)$$

where $S^h_i$ represents the entropy manifested by fast intra-well motion and the second term corresponds to the classical conformational entropy arising from the i=1 . . . N distinct conformations. Here $S^h_i$ is obtained from interpretation of local order parameters, which is model-dependent. The present approach finds its modern roots in the work described in Akke, M., Bruschweiler, R. & Palmer, A. G. *NMR order parameters and free-energy—an analytical approach and its application to cooperative $Ca^{2+}$ binding by calbindin-D(9k). J. Am. Chem. Soc.* 115, 9832-9833 (1993), in which a specific motional model (potential energy function) is used to provide a parametric relationship between what is measured, the squared generalized order parameter, and what is sought, a thermodynamic quantity such as the entropy. See FIG. 4.

FIG. 4*a* demonstrates how there are many potential entropic contributions to the free energy of binding of a ligand by a structured protein. The contribution from the conformational entropy of the protein has historically been difficult to measure and has often been simply assumed to be negligible. In FIG. 4*b*, NMR relaxation is used to measure the local fast dynamical disorder at dozens of methyl groups throughout the calmodulin molecule (represented as spheres). In FIG. 4*c*, changes in dynamics are interpreted, in a model-dependent way, as changes in conformational entropy. This view is supplemented by a model-independent interpretation. Both views support the general conclusion that changes in the conformational entropy of calmodulin upon binding target domains contribute significantly to the free energy of binding and that this contribution varies considerably across a family of domains having roughly the same binding affinity but vastly different thermodynamic origins.

A simple harmonic oscillator treatment was selected to make this connection. Li, Z., Raychaudhuri, S. & Wand, A. J. *Insights into the local residual entropy of proteins provided by NMR relaxation. Prot. Sci.* 5, 2647-2650 (1996). It is important to note that the absolute entropies obtained in this way are very dependent on the details of the potential energy function but that differences in entropy calculated from changes in $O^2$ are fairly insensitive to the model used. Li, Z, et al. (1996); Lee, A. L. et al. *Temperature dependence of the internal dynamics of a calmodulin peptide complex. Biochemistry* 41, 13814-13825 (2002). As the reference state for obtaining $\Delta S_{conf}$ we use calcium-saturated calmodulin. The second term of equation (2) represents classical entropy arising from the local heterogeneity of side-chain conformers. This can be manifested on a range of timescales. Some methyl sites exhibited slowly interconverting conformational heterogeneity on the chemical shift timescale. This was interpreted as classical entropy with the population of each state ($p_i$) estimated from the intensity of cross peaks. This contributed less than 2% of the estimated change in conformational entropy due to binding. It has also been shown that fast motion between rotamer wells contributes significantly to low $O^2_{axis}$ parameters. Lee, A. L. et al. (2002). This also represents conformational entropy and was estimated using a previously described model. Id. This resulted in a roughly constant 15% of the total conformational entropy. Further details of the calculation are provided in Table 4, below.

TABLE 4

| | $-T\Delta S_{conf}$[a] | $TS_{conf}$[a] | $TS_{harm}$[b] | $TS_{rotamer(fast)}$[c] | $TS_{rotamer(slow)}$[c] |
|---|---|---|---|---|---|
| CaMKKα(p) | +63.5 | 705.6 | 597.9 | 98.3 | 9.4 |
| smMLCK(p) | +54.9 | 714.1 | 596.6 | 95.8 | 21.7 |
| CaMK1p | +66.0 | 703.0 | 593.4 | 94.7 | 15.0 |
| PDE(p) | +24.9 | 744.2 | 620.6 | 108.6 | 14.9 |
| eNOS(p) | +46.1 | 723.0 | 605.1 | 101.3 | 16.6 |
| nNOS(p) | +15.9 | 753.1 | 618.3 | 110.1 | 24.8 |
| Free CaM[a] | 0.0 | 769.0 | 640.2 | 125.8 | 3.1 |

[a]The total change in conformational entropy of calmodulin upon binding a target domain is calculated as the sum of three terms: $\Delta S_{conf} = \Delta S_{harm} + \Delta S_{rotamer(fast)} + \Delta S_{rotamer(slow)}$. Free CaM is the reference state. Absolute entropies are shown to indicate relative magnitudes. The actual calculation is effectively based on pair-wise differences. All values are in kJ/mol at 308 K.

[b]Changes in conformational entropy expressed as motion within a rotameric well on the fast time scale(<~8 ns) are modeled using a simple harmonic oscillator. The absolute value of the entropy of the harmonic oscillator is model-dependent. However differences in calculated entropy derived from motion of the same oscillator are relatively robust. The change in the entropy reflected by the change in the motion of each methyl symmetry axis was estimated using $\Delta S_{harm} = -18 \times \Delta O^2_{axis}$ J $mol^{-1}$ $K^{-1}$. See Li et al.[3] for further details of the model. The local entropy changes were totaled for all measured methyl sites to give $\Delta S_{harm}$. This assumes independent motion and likely results in an overestimation.

[c]Classical entropy derived from population of more than one rotameric state is captured by $\Delta S_{rotamer(fast)}$ and $\Delta S_{rotamer(slow)}$. Each site of slowly interconverting conformational heterogeneity was interpreted in the context of a classical local Boltzmann weighted partition function. Populations were estimated from the intensity of the corresponding cross peaks. This results in an additional though relatively small contribution to the conformational entropy (~2%). Each site conformational heterogeneity on the fast timescale was also interpreted using a classical Boltzmann equation. It is well known from theory[4], experiment[4,5] and molecular dynamics simulations[6] that minor rotamer states are increasingly sampled as the $\Delta O^2_{axis}$ decreases. The relationship between population of the major rotamer state and order parameter is based upon the simulations of Lee et al[4] where one major conformation and two energetically equivalent minor conformations are present. This results in an additional relatively constant contribution to the conformational entropy (~15%).

The Conformational Entropy of Binding

Figure 2:
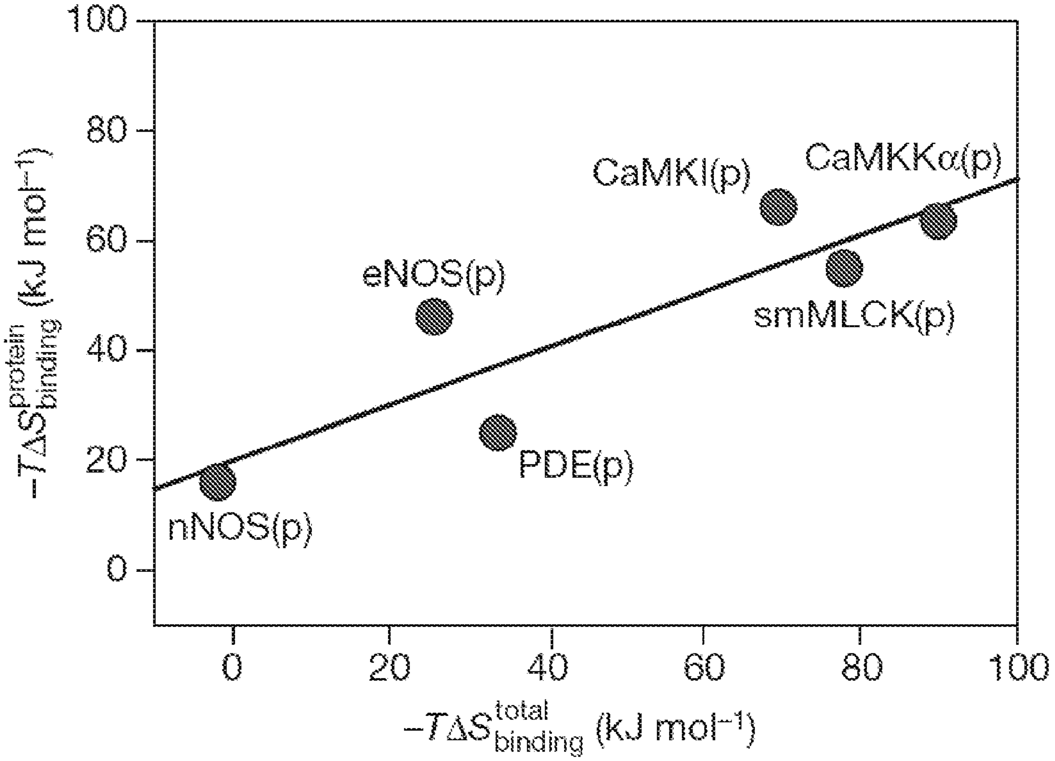
FIG. 2 depicts the correlation of the change in conformational entropy of calmodulin with the change in the total entropy of binding of a target domain.

The simple and direct interpretation of changes in dynamics as changes in conformational entropy is model-dependent and is therefore somewhat sensitive to the underlying accuracy of the model used. In addition, the presence of correlated motion in the packed protein interior will tend to result in an overestimate when interpreting each dynamic probe as independent (that is, by simple summation, equation (2), supra). Notwithstanding these limitations, the changes in the conformational entropy of calmodulin on binding to the six peptides, obtained by simple summation of the individual local entropies, shows a remarkable linear correlation ($R^2$=0.78) with the corresponding entropy of binding (FIG. 2). Taken at face value, half of the binding entropy is reflected in the motion of the methyl-bearing amino acid side chains. There is no a priori reason for such a correlation. However, the linearity of the correlation implies that either the change in the conformational entropy of calmodulin on binding a target domain is a major contribution to the binding entropy or that the various sources of entropy change in concert (see equation (1), supra). Regardless, it seems that the conformational entropy of calmodulin can vary sufficiently to impact the free energy changes arising from high-affinity protein associations. This model-dependent interpretation of the entropic significance of the observed changes in dynamics across the calmodulin complexes is buttressed by a relatively model-independent analysis described below.

Referring to FIG. 2, the change in conformational entropy was estimated using equation (2), as described in Methods (infra) and elsewhere herein. Propagation of measurement error in fitted order parameters results in uncertainties in conformational entropy less than the size of the symbols used. The fitted linear correlation coefficient ($R^2$) of conformational entropy versus the entropy of binding is 0.78 with a slope of 0.51.

The binding of smMLCK(p) to CaM results in a distribution of $O^2_{axis}$ parameters that is remarkable for its distinct clustering into three apparent classes of motion. Lee, A. L. & Wand, A. J. *Microscopic origins of entropy, heat capacity and the glass transition in proteins*. Nature 411, 501-504 (2001).

The sum of the distributions of methyl group $O^2_{axis}$ parameters in the six calmodulin complexes is shown in FIG. 3a. The large number of samplings (n=404) provides for robust fitting of the distribution to the sum of three Gaussians. The best-fitted line is shown ($R^2$=0.94 and P<0.0001) and the nine best-fitted parameters are provided in Table 5, below.

TABLE 5

Description of the Motional Modes of Calmodulin[a]

|  | J-class | α-class | ω-class |
| --- | --- | --- | --- |
| Intensity (A) | 31.6 ± 2.3 | 33.2 ± 4.2 | 33.4 ± 2.6 |
| Center (C) | 0.36 ± 0.013 | 0.60 ± 0.010 | 0.79 ± 0.013 |
| Breadth (W) | 0.11 ± 0.014 | 0.054 ± 0.011 | 0.083 ± 0.0013 |

Figure 3:
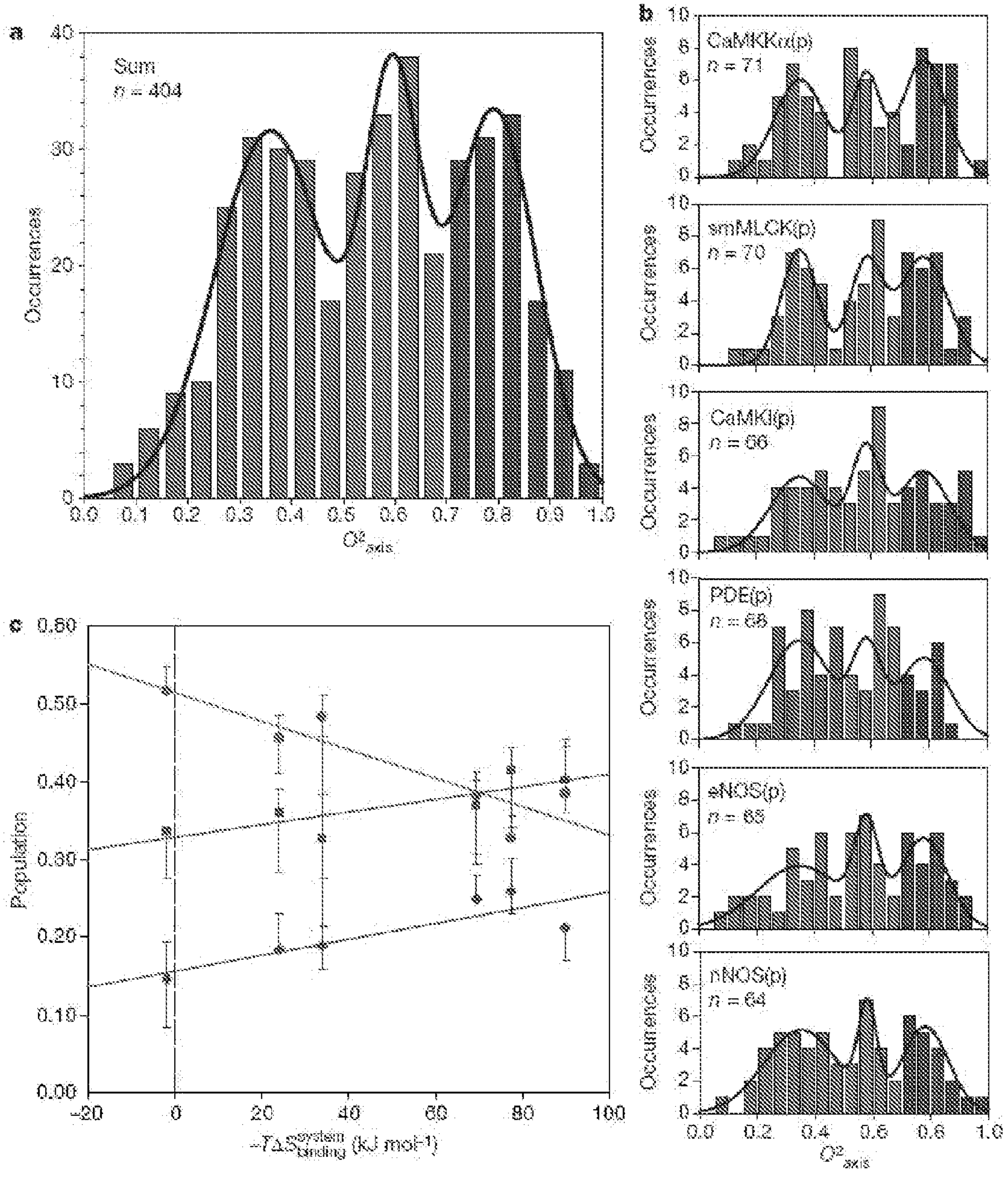
FIG. 3 shows the distribution of the amplitude of methyl-bearing side-chain motion of calmodulin in complex with target domains, and correlation with the change in total entropy of binding.

[a]Best fitted parameters with estimated standard error for 3-Gaussian description of the summed methyl group $O^2_{axis}$ distribution of the six calmodulin complexes (see FIG. 3). Occurrences ($O^2_{axis}$) = $A_J \exp[((-O^2_{axis} - C_J)/W_J)^2/2] + A_\alpha \exp[((-O^2_{axis} - C_\alpha)/W_\alpha)^2/2] + A_\omega \exp[((-O^2_{axis} - C_\omega)/W_\omega)^2/2]$ where $A_i$, $C_i$, and $W_i$ define the population, centre and breadth of the J, α, and ω classes of motion.

The summed distribution yielded fitted 3-gaussian distributions centred on $O^2_{axis}$ values of 0.35 (large 'amplitude' motion), 0.58 (intermediate 'amplitude' motion) and 0.78 (highly restricted motion). Using these centres, the distributions of $O^2_{axis}$ parameters in each of the six physiologically relevant calmodulin complexes are also satisfactorily described by a sum of three gaussians (FIG. 3). The relative populations of these motional classes in calmodulin vary considerably across the six complexes.

FIG. 3a, provides a histogram of the sum of the $O^2_{axis}$ parameter distributions of calmodulin in the six individual complexes obtained at 35° C. The solid line represents the best-fitted solution to a 3-gaussian distribution with all nine parameters fitted. The best-fitted parameters are given in Table 5, supra. FIG. 3b provides histograms of the $O^2_{axis}$ parameter distributions of calmodulin in the individual complexes. The solid lines represent fitted 3-gaussian distributions centred on $O^2_{axis}$ values of 0.35 (J-class, red), 0.58 (α-class, green) and 0.78 (ω-class, blue). The relative populations of each class were derived from the fitted 3-gaussian distributions for each complex. FIG. 3c provides a correlation of the change in population of the J, α and ω classes with the $-T\Delta S_{bind}$ have fitted linear correlation coefficients ($R^2$) of −0.83, +0.74 and +0.71, respectively. Correlation of the number of sites assigned to each class by simple binning, as colour-coded, yielded similar results, as shown in Table 6, below. In FIG. 3, error bars reflect the variation of the population of each motional class that results from an increase or decrease in the measured $O^2_{axis}$ values by two standard deviations.

TABLE 6

Mode Populations Determined By A Number Of Observations[a]

|  | CaMKKα(p) | smMLCK(p) | CaMKI(p) | PDE(p)[a] | eNOS(p) | nNOS(p) | Slope[c] (mol J$^{-1}$) | $R^{2c}$ |
| --- | --- | --- | --- | --- | --- | --- | --- | --- |
| % J | 35 | 36 | 38 | 46 | 38 | 45 | −0.090 | 0.80 |
| % α | 30 | 30 | 30 | 33 | 30 | 25 | +0.045 | 0.61 |
| % ω | 35 | 34 | 32 | 20 | 33 | 30 | +0.041 | 0.68 |

[a]Instead of taking the area under each of the Gaussian peaks, we can simply take the percentage of counts in each class. Sites with $O^2_{axis}$ values from $0 > O^2_{axis} \geq 0.5$ are taken to be in the J-class. The α-class corresponds to sites $0.5 > O^2_{axis} \geq 0.7$ and the ω-class is comprised of site $0.7 > O^2_{axis}$. The populations of the modes were determined using these cutoffs. This method is clearly unsatisfactory for the PDE complex at the interface between the α and ω classes. This complex is excluded from the linear regression. The difference between this simple approach and the direct fitting of the Gaussian distribution (Supplementary Information Table 5) is that the J-band and ω-band are both less populated by about 4% and the α-band gains about 8% when the former method is used. This is because the number of observations method truncates the tails of the Gaussian distribution of the central peak.
[b]The PDE complex is excluded from the linear regression of populations versus total binding entropy.
[c]Slope and $R^2$ from linear regression of mode population against total binding entropy (see Supplementary Information Table 2).

Although the distinctive grouping of order parameters, seen across all six complexes studied here, is often obscured in other proteins (Best, R. B., Clarke, J. & Karplus, M *The origin of protein sidechain order parameter distributions*. J. Am. Chem. Soc. 126, 7734-7735 (2004)), the motional origin of these classes is clear. In the case of calmodulin, two fundamental types of motion occurring on the sub-ns timescale are involved: motion within a rotamer well, and motion between rotamer wells of side-chain torsion angles. Lee, A. L. et al. *Temperature dependence of the internal dynamics of a calmodulin peptide complex*. Biochemistry 41, 13814-13825 (2002). It has been shown that the class of large amplitude motion centred on a $O^2_{axis}$ value of −0.35 generally involves a significant contribution from rotameric interconversion on the nanosecond or faster timescale because it leads to a significant averaging of scalar coupling (J) constants. Lee, A. L. et al. (2002). More recent experimental results (Chou, J. J., Case, D. A. & Bax, A. *Insights into the mobility of methyl-bearing side chains in proteins from $^3J_{CC}$ and $^3J_{CN}$ couplings*. J. Am. Chem. Soc. 125, 8959-8966 (2003)) and theoretical simulations (Best, R. B., Clarke, J. & Karplus, M. *What contributions to protein side-chain dynamics are probed by NMR experiments? A molecular dynamics simulation analysis*. J. Mol. Biol. 349, 185-203 (2005)) suggests this to be general. The class of motion at the other extreme is centred on an $O^2_{axis}$ value of −0.8, which represents highly restricted motion within a rotamer well. The class of moderate motion centred on an $O^2_{axis}$ value of −0.6 involves little detectable rotamer interconversion and is restricted to motion within a single rotamer well. The precise value reflects intra-well motion and the effects of superposition of similar motion about connected torsion angles. We have termed these groupings the J-, ω- and α-classes of motion, respectively. Igumenova, T I., Frederick, K. K. & Wand, A. J. *Characterization of the fast dynamics of protein amino acid side chains using NMR relaxation in solution. Chem. Rev.* 106, 1672-1699 (2006).

The fractional populations of each motional class, derived from the fitting of the observed distributions of $O^2_{axis}$ parameters, in the six complexes reveal a surprising correlation with the change in total system entropy for binding (FIG. 3*c*). The population of the J-class is negatively correlated with the entropic contribution (−TΔS) to the free energy of binding. The populations of the ω- and α-classes are positively correlated. The correlations are remarkably linear for all three classes. A similar correlation is found by simply taking the percentage of counts in each class, as colour-coded and as described in Table 7, below.

TABLE 7

Mode populations of the CaM complexes determined from fitting of $O^2$ axis individual distributions.[a]

| | % J | % α | % ω |
|---|---|---|---|
| CaMKKα(p) | 38.5 (0.0, 7.0) | 21.3 (4.2, 2.8) | 40.3 (4.2, 4.2) |
| smMLCK(p) | 32.7 (0.0, 3.0) | 25.9 (2.9, 4.3) | 41.4 (2.9, 7.1) |
| CaMKI(p) | 38.2 (7.6, 3.0) | 24.8 (0, 3.0) | 37.0 (3.0, 7.6) |
| PDE(p) | 48.3 (10, 2.9) | 18.9 (2.9, 8.6) | 32.8 (12.9, 11.4) |
| eNOS(p) | 45.6 (4.6, 3.1) | 18.4 (0, 4.6) | 36.0 (3.1, 7.7) |
| nNOS(p) | 51.6 (3.1, 0.0) | 14.7 (6.3, 4.7) | 33.7 (0, 6.3) |
| Slope[b] (mol $J^{-1}$) | −0.180 | +0.102 | +0.081 |
| $R^2$ | 0.83 | 0.74 | 0.71 |

[a]$O^2_{axis}$ distributions of each complex were fitted to the three Gaussian distribution of Table 3 (supra) using the fixed centres determined as described in that table. Populations were determined from the area under each fitted Gaussian curve. Reliability estimates of the obtained populations were obtained by propagating two standard deviations of the estimated standard error for the individual $O^2_{axis}$ parameters determined by Monte Carlo analysis of the fitting of the primary relaxation data. This results in asymmetric error bars (shown in parentheses).

[b]Slope and $R^2$ from linear regression of mode population against total binding entropy (see Table 2, supra).

Both views provide a direct, relatively model-insensitive indication that the conformational entropy of calmodulin changes in concert with the change in the entropy of binding and that this variation can, in part, be identified with the motional class of the involved side chains.

Empirical Calibration

The presence of a linear correlation between the apparent change in conformational entropy and $\Delta S_{bind}$ is a compelling indication of the importance of the former. In an another embodiment of the invention experimentally obtained measurements of local dynamics were used as estimates of local disorder and an empirical scaling between them was established. The aim-was to effectively solve for each term of equation (1). An essential component of this approach is knowledge of the entropic contribution of the target domains to the binding process.

Dynamics of the Target Domains in Complex with CaM

Using deuterium NMR relaxation methods, fast motion of the methyl-bearing side-chains of the target domains in the six CaM complexes were examined. Muhandiram, D. R. et al., *Measurement of H-2 T-1 and T-1p relaxation-times in uniformly C-13-Labeled and fractionally H-2-labeled proteins in solution. J. Am. Chem. Soc.* 117, 11536-11544 (1995).

Figure 5:
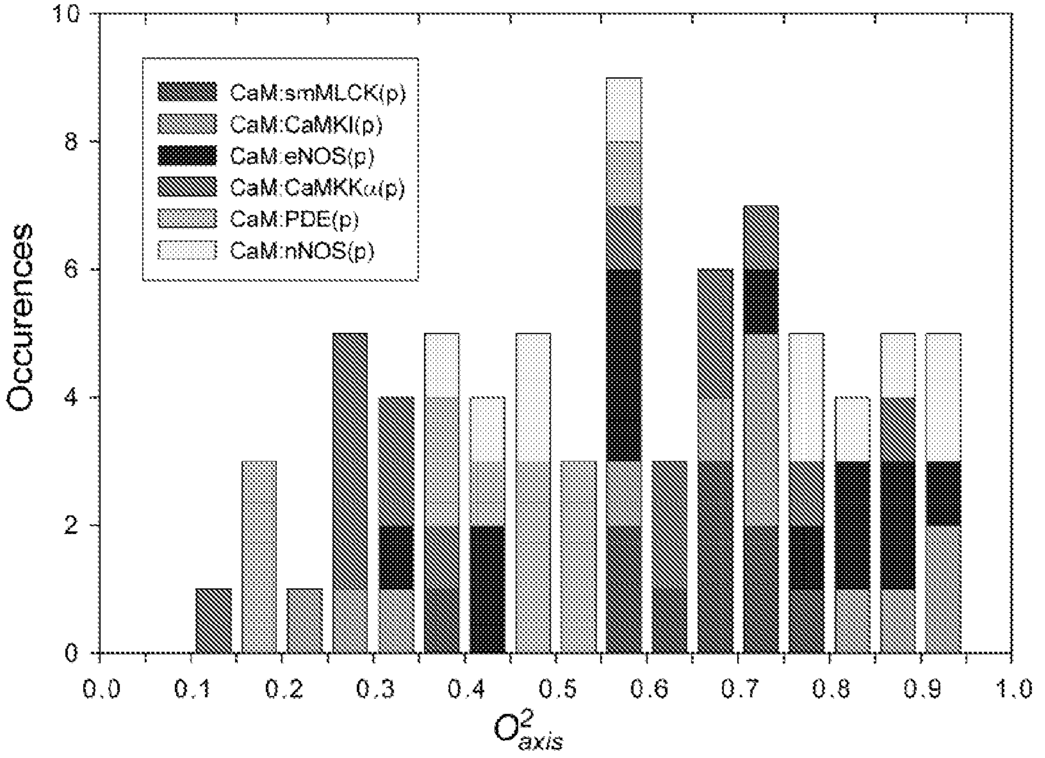
FIG. 5 shows the distribution of methyl symmetry axis generalized order parameters ($O^2_{axis}$) for target domains bound to calcium-saturated calmodulin (CaM)

All bound target domain methyl resonances are well resolved in $^{13}C$-single quantum heteronuclear correlation ($^{13}C$-HSQC) NMR spectra and deuterium relaxation parameters could be measured with high precision. The 76 methyl order parameters from 52 residues of the target domains in the six complexes are heterogeneously distributed with $O^2_{axis}$ values ranging from 0.13 to 0.95 (FIG. 5).

Variable Dynamics at the Interface

High resolution structures of all but the complex with PDE are known and indicate that the methyl bearing side-chains of the target domains are distributed throughout the CaM-peptide interface providing an excellent system to examine the intricacies of structure-dynamics relationships. Key features of CaM-peptide complexes are the so-called peptide anchor residues that localize to hydrophobic pockets formed by the amino and carboxy-terminal domains of CaM. Typically, one anchor residue is aromatic (Trp or Phe) and the other aliphatic. Anchor residues are believed to be essential for complex formation because calcium activation induces structural changes in CaM that expose numerous methionine and branched aliphatic residues to solvent that subsequently bind the hydrophobic target domain anchors. In order to better understand the relationship between the methyl dynamics of CaM and the methyl dynamics of bound peptides and to identify residues with perturbed dynamics that might provide insight to the role of dynamics in binding phenomena, we compared the order parameters with the residue-specific order parameters determined from our entire CaM data set (Table 8). It was found that motion of methyl-bearing side chains is not uniformly affected by binding.

TABLE 8

Average $O^2_{axis}$ values from six CaM/peptide complexes

| | $O^2_{axis}$ | n |
|---|---|---|
| Ala Cβ | 0.803 ± 0.202 | 44 |
| Ile Cγ2 | 0.727 ± 0.095 | 46 |
| Ile Cδ1 | 0.502 ± 0.205 | 45 |
| Leu Cδ1/2 | 0.437 ± 0.164 | 90 |
| Met Cϵ | 0.395 ± 0.193 | 51 |
| Thr Cγ2 | 0.578 ± 0.146 | 41 |
| Val Cγ1/2 | 0.616 ± 0.136 | 72 |
| Total | 0.563 ± 0.212 | 389 |

Figure 6:
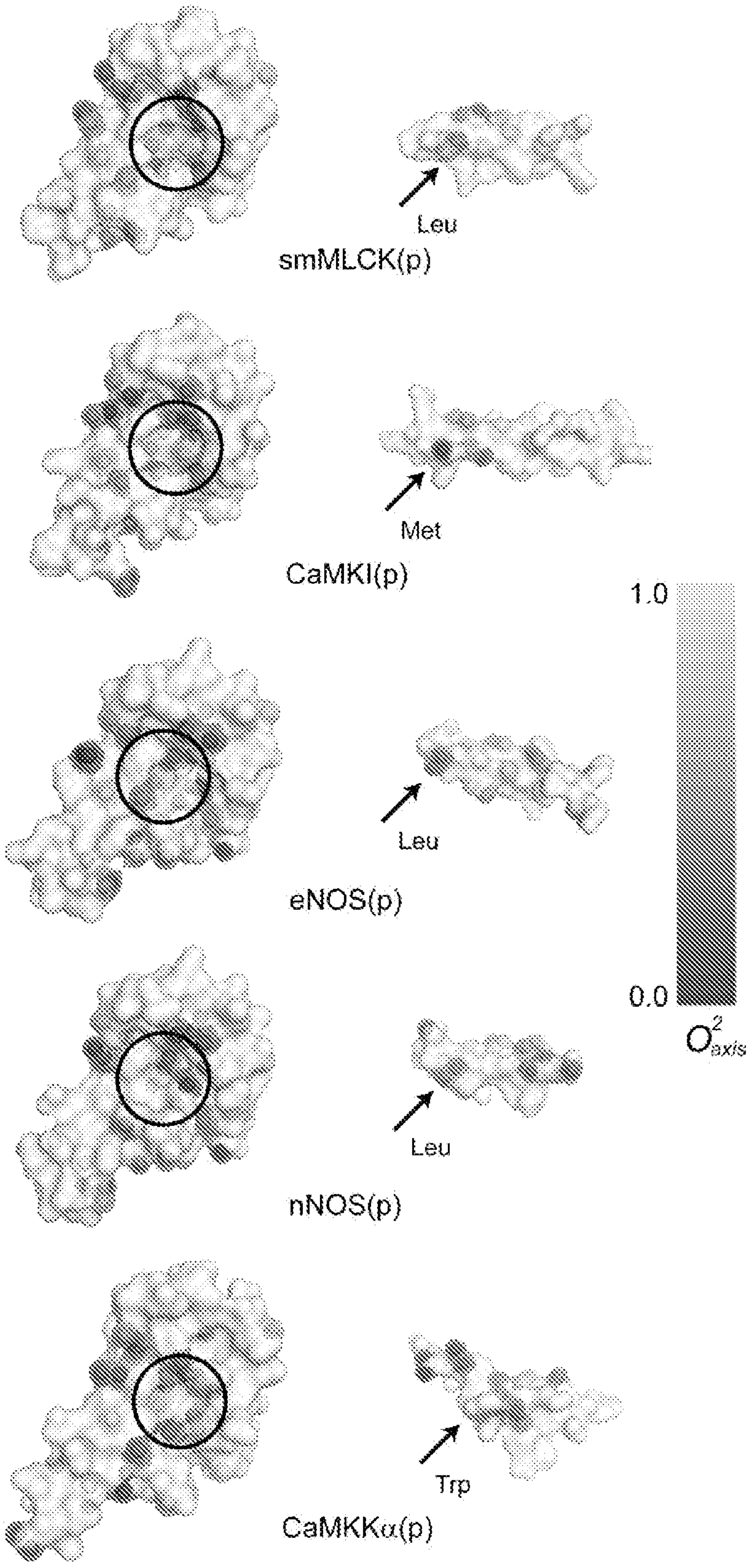
FIG. 6 shows the dynamical character of the hydrophobic anchor in the N-terminal domain of CaM where circled areas indicate the hydrophobic pockets of CaM and indicate highly restrained motion at the base of the pocket and more mobility along sides. The arrows point to the so-called anchor residues.

Emphasis was placed on the dynamical character of the aliphatic side-chain anchors that are localized to the amino-terminal domain of CaM (FIG. 6). Most aliphatic peptide side chains traditionally identified as anchor residues are more dynamic than one might expect. Specifically, the $O^2_{axis}$ values of eNOS(p) and nNOS(p) leucine δ methyls and the CaMKI (p) methionine ϵ methyl are at or below the residue-specific averages from our CaM data set. Sequence alignment shows PDEs(p) does not have the canonical 1-14 spacing of anchor residues and suggests it to be either PDEs(p)V17 (1-12 spacing) or PDEs(p)L20 (1-15 spacing). The dynamics of this complex suggests that PDEs(p) V17 is the hydrophobic anchor because the PDEs(p)L20 is a highly dynamic residue ($O^2_{axis}$=0.165). Consistent with the dynamics of eNOS(p), nNOS(p), and CaMKI(p), the $O^2_{axis}$ values of PDEs(p)V17 are also significantly less than average. With the exception of the $O^2_{axis}$ values of leucine Cδ1/2 in the smMLCK(p) complex, the overall trend appears to indicate binding within the pocket does not significantly confine the motion of the anchor residues. This unexpected result provides some insight to why mutations designed to significantly impact a particular binding event sometimes have diminished, or unintended consequences; part of the affinity is manifested in the local entropy of the interacting groups.

Complex formation results in a striking pattern of the dynamics of the CaM methyl-bearing residues that form the binding pocket (127, L32, M51, I52, V55, I63, and M71). For example, in every complex I27δ and I63δ exhibit relatively restricted motion with an average $O^2_{axis}$ of 0.695 (n=12), which is 0.193 greater than the average within our CaM complex data set. On the other hand, the $O^2_{axis}$ parameters of L32, M51, I52, V55, and M71 are significantly lower than the average of all such residues within our CaM data set, indicating that these side-chains are relatively more flexible. Interestingly, we observe a similar pattern in the CaM residues found in the carboxy-terminal pocket that bind aromatic peptide anchor residues. Specifically, two residues, 1100δ and V1369γ1/γ2, are greatly rigidified in all complexes (average $\Delta O^2_{axis}$=0.105, n=15) whereas the motion of L105, I125, and A128 is only slightly less than the corresponding residue specific averages (average $\Delta O^2_{axis}$=−0.044, n=25). Together, this suggests that complex formation does not induce a uniform general reduction in the amplitude of side-chain motion throughout the hydrophobic pockets, but rather that specific groups experience increased rigidity while others retain greater motional freedom. Certainly, such dynamic selectivity is precedent for extending the view of hot spot interactions to include resolution of dynamical (entropic) effects from specific enthalpic contributions to the binding free energy. Clackson, T. & Wells, J. A., *A hot spot of binding energy in a hormone-receptor interface. Science* 267, 383-386 (1995).

Calibration of the "Entropy Meter"

Initially estimates of the conformational entropy of the target domains to the free energy of binding to CaM was obtained using the simple harmonic oscillator model. Li, Z., Raychaudhuri, S., & Wand, A. J., *Insights into the local residual entropy of proteins provided by NMR relaxation. Prot. Sci.* 5, 2647-2650 (1996). It is assumed that the dynamics of the free unstructured target domain are uniform and correspond to an $O^2_{axis}$ of 0.1. In calculating the corresponding entropy we also correct for the fact that fast motion between rotamer wells contributes significantly to $O^2_{axis}$ and also represents conformational entropy. This was estimated using a previously described model. Lee, A. L. et al., *Temperature dependence of the internal dynamics of a calmodulin peptide complex. Biochemistry* 41, 13814-13825 (2002). There is no micro-heterogeneity of side-chain conformations of the bound target domains evident in their $^{13}$C-HSQC spectra. Such heterogeneity would correspond to conformational entropy contributed by states that are not averaged on the NMR chemical shift timescale. Such micro-heterogeneity was observed in CaM in some of the complexes.

To obtain an empirical calibration of the dynamical proxy of conformational entropy in the calmodulin system, the entropy of binding is first expressed in terms of contributions from calmodulin, the target domains and solvent:

$$\Delta S_{bind}=\Delta S_{conf}(CaM)+\Delta S_{conf}(\text{target})+\Delta S_{solv}+\Delta S_{RT} \quad (3)$$

The changes in rotational and translational entropy of CaM and the peptide ($\Delta S_{RT}$) have been grouped. The similarity in peptide lengths, the structures of the complexes, and the binding affinities suggest that $\Delta S_{RT}$ is essentially constant across the five complexes to be considered (the structure of CaM:PDE(p) complex remains unknown). Not be limited to one theory, it is postulated that the true contribution of changes in the conformational entropy of CaM and the target domains is linearly related to that estimated from NMR relaxation in methyl groups:

$$\Delta S_{conf}(CaM)=m_1\Delta S'_{conf}(CaM)+b_1;$$
$$\Delta S_{conf}(\text{target})=m_2\Delta S'_{conf}(\text{target})+b_2 \quad (4)$$

In equation (4), ΔS' indicates the apparent change in conformational entropy calculated as above and without empirical calibration (see Methods). The constants ($b_1$ and $b_2$) reflect potential contributions in entropy from sources that are not sensed by the type of motional probes used here. This comprises, for example, vibrational entropy that involves motion that does not average the angle of the methyl symmetry axis with the magnetic field. It further comprises of contributions not included in the calculation of solvent entropy such as that arising from the electrostriction of water by solvation of explicit charge (see below). Not to be limited to one theory, $b_2$ is taken to be the same for all target peptides. The scaling factors ($m_1$ and $m_2$) are set equal to a single constant m. Substitution into equation (3) and rearrangement leads to the prediction of a linear relationship between the difference of the total binding entropy and the solvent entropy and the apparent change in conformational entropy measured by NMR relaxation:

$$\Delta S_{bind}-\Delta S_{sol}=m[\Delta S'_{conf}(CaM)+\Delta S'_{conf}(\text{target})]+(b_1+b_2)+\Delta S_{RT} \quad (5)$$

To compare dynamics in the various complexes, we employ a normalization procedure to account for variation in the number of methyl sites in CaM whose motion could be quantified and to account for the fact that, although fully resolved, the number of residues in the target domains ranges between 20 and 26. A simple average was employed. The apparent change in conformational entropy was then calculated as above. To complete the solution of equation (5), the binding entropies obtained by isothermal titration calorimetry were used and calculated the change in solvent entropy using the known structures of free CaM and the five complexes. Kainosho, M. et al., *Optimal isotope labelling for NMR protein structure determinations. Nature* 440, 52-57 (2006); Aoyagi, M et al., *Structural basis for endothelial nitric oxide synthase binding to calmodulin. The EMBO journal* 22, 766-775 (2003); Meador, W. E., Means, A. R., & Quiocho, F. A., *Target enzyme recognition by calmodulin:* 2.4 *A structure of a calmodulin-peptide complex. Science* 257, 1251-1255 (1992); Clapperton, J. A. et al., *Structure of the complex of calmodulin with the target sequence of calmodulin-dependent protein kinase I: studies of the kinase activation mechanism. Biochemistry* 41, 14669-14679 (2002); Osawa, M. et al., *A novel target recognition revealed by calmodulin in complex with Ca2+-calmodulin-dependent kinase kinase. Nat. Struct. Biol.* 6, 819-824 (1999); Valentine, K. G. et al., *The crystal structure and internal dynamics of calmodulin complexed with the calmodulin binding domain of neuronal nitric oxide synthase. Biochemistry*, submitted (2007). The empirically determined relationship between changes in accessible surface area and the entropy of solvent is employed. Hilser, V. J. et al., *A statistical thermodynamic model of the protein ensemble. Chem. Rev.* 106, 1545-1558 (2006). The change in solvent entropy by assuming an extended fully solvated structure for the dissociated domains (see Methods) was calculated. Analysis of the target domain sequences indicated that CaMKKα(p) is exceptionally hydrophobic. Indeed, hydrophobic cluster analysis illuminates a hydrophobic patch that is comprised of seven hydrophobic residues and suggests that the dissociated domain exists in a collapsed, less hydrated state than is assumed in the calculation of solvent entropy based on an extended chain. Gaboriaud, C. et al., *Hydrophobic cluster analysis: an efficient new way to compare and analyse amino acid sequences. FEBS letters* 224, 149-155 (1987). Of the five CaM complexes with known structure, CaMKKα(p) is the only target domain showing this feature. The surface area of a sphere of equivalent volume of the side-chains in the putative hydrophobic cluster was used as a basis for the solvent entropy calculation. The calculated change in accessible surface area and associated solvation entropies are given in Table 9, below. A further correction for the reduction in conformational entropy of the compact free CaMKKα(p) target domain was also applied (see Methods). Not to be limited by one theory, the isothermal titration calorimetry of the formation of this complex is simple and unremarkable and does not indicate the presence of a more complex equilibrium involving the disassembly of aggregates of the target, for example. Marlow, M. S. & Wand, A. J., *Conformational dynamics of calmodulin in complex with the calmodulin-dependent kinase kinase alpha calmodulin-binding domain. Biochemistry* 45, 8732-8741 (2006).

would result in a positive contribution to the binding free energy (see Equation 3). Not to be limited to one theory, this apparent discrepancy is most easily explained by recognizing that the formation of the each of the complexes results in the burial of 6 charged side-chains through the formation of ion pairs. The removal of charge from bulk water will result in a significant increase in solvent entropy. The degree of electrostriction in the free state can be estimated from the pressure dependence of the formation of the CaM:CaMKI complex, which has been measured using hydrogen exchange based methods. Kranz, J. K. et al., *Dissection of the pathway of molecular recognition by calmodulin. Biochemistry* 41, 2599-2608 (2002). Comparison to solvent entropy values for model charged species suggests that this effect can easily overcome the predicted positive contribution to the free energy of binding by $\Delta S_{RT}$. Marcus, Y., *Ionic volumes in solution. Biophysical chemistry* 124, 200-207 (2006).

Insights into the Role of Protein Entropy in Binding

The relationship between the change in the conformational entropy of CaM and the target domains and the total entropy of binding is quantitatively revealed. The changes in confor-

TABLE 9

Estimation of solvent binding entropy based on changes in accessible surface area[a]

| Complex | Polar ASA CaM ($Å^2$) | Apolar ASA CaM ($Å^2$) | Polar ASA free target[h] ($Å^2$) | Non-Polar ASA target[h] ($Å^2$) | Polar ASA bound target ($Å^2$) | Non-polar ASA bound target ($Å^2$) | Change in Solvent Entropy[i] (kJ/mol) |
|---|---|---|---|---|---|---|---|
| Free CaM[b] | 5237 | 4449 | n/a | n/a | n/a | n/a | n/a |
| CaM:CaMKKα(p)[c] | 4410 | 3771 | 1642 (1610)[j] | 2155 (1745)[j] | 492 | 776 | 322 (268)[j] |
| CaM:smMLCK(p)[d] | 4049 | 3845 | 1559 | 1395 | 470 | 279 | 287 |
| CaM:CaMKI(p)[e] | 3978 | 3697 | 1970 | 2000 | 582 | 653 | 346 |
| CaM:eNOS(p)[f] | 4140 | 3596 | 1460 | 1399 | 453 | 365 | 303 |
| CaM:nNOS(p)[g] | 4366 | 3980 | 1375 | 1527 | 325 | 380 | 263 |

[a]Accessible surface area calculations performed with the program VMD, see text for details.
[b]Based on the structure of free calcium-saturated calmodulin determined by Lu et al. (PDB code 1XO2).
[c]Based on the structure determined by Osawa et al. (PDB code 1CKK).
[d]Based on the structure determined by Meador et al. (PDB code 1CDL).
[e]Based on the structure determined by Clapperton et al. (PDB code 1MXE).
[f]Based on the structure determined by Aoyagi et al. (PDB code 1NIW).
[g]Based on the structure determined by Valentine et al. (PDB code 2O60).
[h]Based on an extended chain structure with phi and psi angles of −140 and 130 degrees, respectively. Does not include the amino-terminal GS of the peptides; the surface area of these residues is assumed to be highly similar in free and bound states.
[i]Calculated using Equation 8 of Hilser, et al: $\Delta S_{solv} = (0.45 * \Delta ASA_{apolar} * \ln(308/385) + 0.26 * \Delta ASA_{polar} * \ln(308/335)$.
[j]Values in parentheses have been corrected for predicted hydrophobic clustering (see Methods and FIG. 5)

Figure 7:
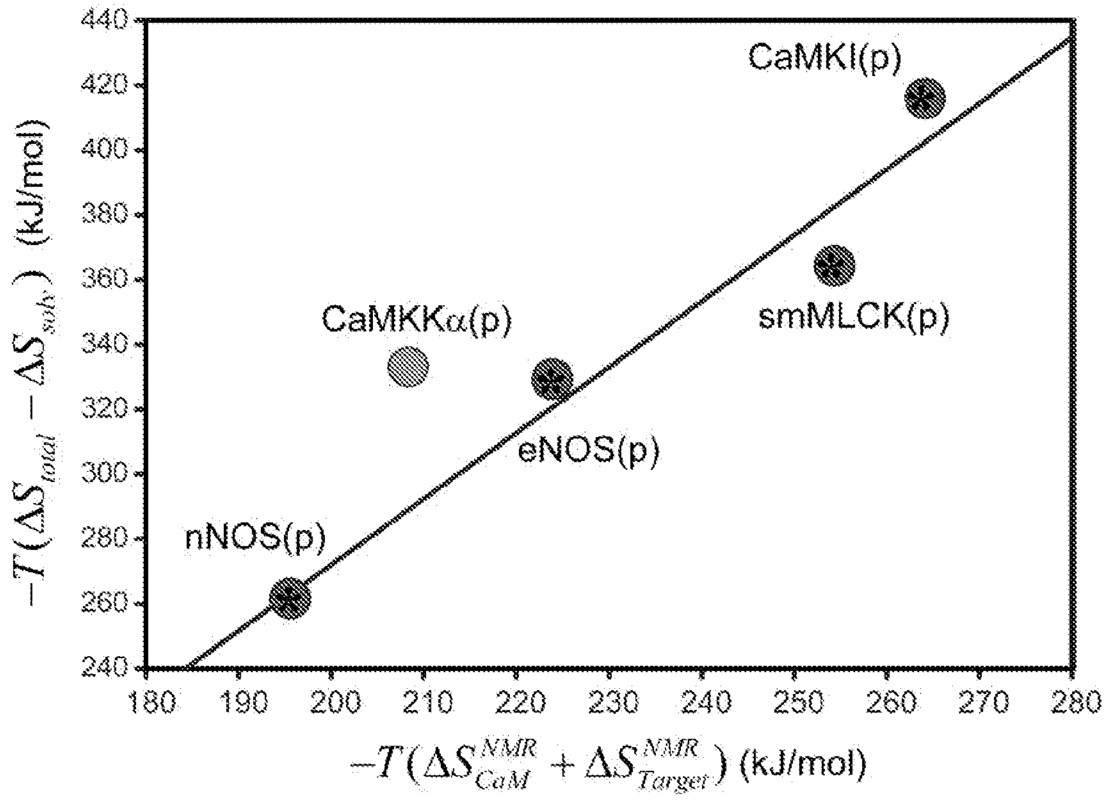
FIG. 7 shows the calibration of the dynamical proxy for protein conformational entropy.

Equation (5) requires a quantitative linear relationship between ($\Delta S_{bind}$-$\Delta S_{sol}$) and ($\Delta S_{conf}$(CaM)+$\Delta S_{conf}$(target)). A linear relationship with regression statistics ($r^2$=0.96) and a slope of 2.03 and an intercept of −140 kJ $mol^{-1}$ is indeed observed (FIG. 7). The slope indicates that the contribution of conformational entropy to the binding of target domains to CaM has been previously underestimated by almost a factor of two. While not intending to be limited to one theory, the quantitative linearity of FIG. 7 strongly suggests that the assumptions underlying equation (5) are largely valid and that a self-consistent view of the origin of the thermodynamics of binding in the calmodulin system has been established. Most important is the apparent validity of employing measures of motion as a proxy for conformational entropy. Furthermore, the quantitative consistency also suggests that the contribution from vibrational entropy (largely contained in the constant intercept) to the overall binding free energy is not variable across the complexes.

Figure 8:
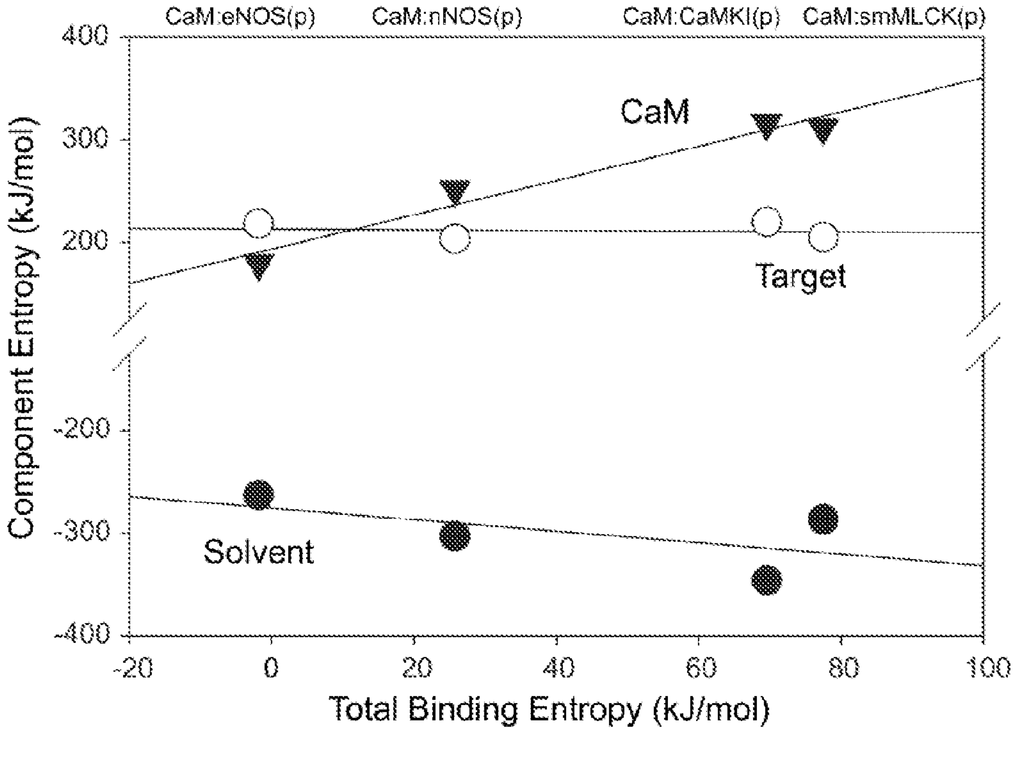
FIG. 8 shows the contributions to the entropy of binding target domains to calcium-saturated calmodulin.

Interestingly, the ordinate intercept of FIG. 7 is negative even though the loss of rotational and translational entropy mational entropy (scaled by m) of the target domains and CaM are large relative to the free energy of binding and are the same magnitude as the solvent entropy (FIG. 8 and Table 10). The change in the conformational entropy of the target domain is only weakly correlated with the binding entropy (FIG. 8). The predicted increases in solvent entropy upon binding are large and favorable but are not significantly correlated with binding entropy (FIG. 8). Thus, although solvent entropy is a powerful general driving force it does not appear to have been utilized in the evolutionary refinement of CaM's affinity for target domains. In contrast, the conformational entropy of CaM is strongly related to the entropy of binding (FIG. 8). Not to be limited to one theory, this interesting segregation may find its roots in the details of the evolution of the target protein calmodulin-binding domains and the need to resolve a complex optimization of structural specificity (molecular recognition) and affinity. In effect, it is the variation of the conformational entropy of calmodulin that "tunes" the free energy of binding.

TABLE 10

Uncalibrated estimate of the conformational entropy of binding based on methyl group dynamics

| Complex | $\Delta\langle O^2_{axis}\rangle$ CaM[a] | $\Delta\langle O^2_{axis}\rangle$ Target[b] | Normalized $\Delta\langle O^2_{axis}\rangle$[c] | $\Delta S_{fast}^{conf}$ (kJ/mol)[d] | $\Delta S_{total}^{conf}$ (kJ/mol)[5] |
|---|---|---|---|---|---|
| CaM:CaMKKαp | 0.096 | 0.329 | 22.632 | 202.054 | 208.354 |
| CaM:smMLCKp | 0.099 | 0.548 | 25.612 | 235.720 | 254.320 |
| CaM:CaMKIp | 0.107 | 0.555 | 28.046 | 252.260 | 264.150 |
| CaM:eNOSp | 0.081 | 0.567 | 23.328 | 210.363 | 223.863 |
| CaM:nNOSp | 0.049 | 0.528 | 19.396 | 173.864 | 195.564 |

[a]Free CaM is the reference state.

[b]$\langle O^2_{axis}\rangle$ of 0.101 was assumed for the free target domain.

[c]The change in methyl dynamics was normalized to the number of amino acids in calmodulin (148), which is constant for all complexes, and the number of amino acids in each target domain (ntd; see Table 1) using the following equation: Normalized $\Delta\langle O^2_{axis}\rangle = (\Delta\langle O^2_{axis}\rangle \text{ CaM} \times 148) + (\Delta\langle O^2_{axis}\rangle \text{ Target} \times \text{ntd})$

[d]Protein conformational entropy change estimated by NMR relaxation. Includes contributions from motion within a rotameric well, modeled using a simple harmonic oscillator and calculated using $\Delta S = \Delta O^2_{axis} \times -18$ J/mol K. Li, Z., Raychaudhuri, S., & Wand, A. J., Insights into the local residual entropy of proteins provided by NMR relaxation. Prot. Sci. 5, 2647-2650 (1996). Population of minor rotamer states on the fast timescale also contributes to the conformational entropy of CaM. The relationship between $O^2_{axis}$ and the population of a single major and two energetically equivalent minor rotamer states was estimated previously. Lee, A. L. et al., Temperature dependence of the internal dynamics of a calmodulin peptide complex. Biochemistry 41, 13814-13825 (2002).

[e]Includes a classical conformational entropy term based on observance minor cross peaks in the slow exchange time regime on the NMR chemical shift time scale.

Nonlimiting Exemplary Biological and Pharmacological Implications

A battery of NMR methods has been employed to characterize the dynamic response of calmodulin to the binding of six target regulatory domains. This view has been interpreted in terms of the changes in conformational entropy of calmodulin on binding. The behaviour of the six physiologically relevant interactions indicates that the conformational entropy of structured proteins can enter very significantly into high-affinity interactions between proteins. Therefore the commonly held view that high-affinity interactions are necessarily energetically dominated by specific structural (enthalpic) interactions must be relaxed to include the structural dynamics and heterogeneity that contributes to conformational protein entropy. Protein entropy can be exploited in the maturation of high-affinity interactions either by biological evolution or by human intervention such as in the design of protein-targeted pharmaceuticals. The preeding results indicate conformational entropy can indeed play a significant part in more complex protein functions such as allostery.

Methods

Sample Preparation and Isothermal Titration Calorimetry

Calmodulin and synthetic peptides and complexes were prepared as described previously (Kranz, J. K. et al. *A direct test of the reductionist approach to structural studies of calmodulin activity: relevance of peptide models of target proteins. J. Biol. Chem.* 277, 16351-16354 (2002)) in 20 mM imidazole (pH 6.5), 100 mM KCl, 6 mM $CaCl_2$ and 0.02% (w/v) $NaN_3$. NMR samples were slightly (~10%) over-titrated with peptide to ensure full complex formation. For isothermal titration calorimetry, calcium-saturated calmodulin (200 μM) was used to titrate dilute solutions of peptide (5-20 μM) to avoid artefacts arising from peptide aggregation. Data were obtained with a VP-isothermal titration calorimeter (Microcal) and analysed with the Origin (v.5) software.

Target domains were expressed as fusion proteins with thioredoxin-6His-tag ("6His" disclosed as SEQ ID NO: 7). In many cases, the over-expressed protein was either insoluble or found to be partially degraded during cell lysis, necessitating extraction under denaturing conditions. Fusion proteins were partially purified with His•Bind (Novagen) resin, using a step-wise reduction of denaturant (to 2M) prior to elution. Excess CaM and 2 mM CaCl2 were added to enriched fractions in order to increase recovery during final dialysis to aqueous conditions. Fusion proteins were cleaved with thrombin (Sigma) typically for 2-4 hours at room temperature. No activity of thrombin toward CaM was observed in a 10-fold over digest. Cleaved fusion protein was removed with His•Bind resin and the CaM:peptide complex was purified/buffer exchanged by gel filtration. Calmodulin was prepared as described previously (Kranz, J. K. et al., A direct test of the reductionist approach to structural studies of calmodulin activity: relevance of peptide models of target proteins. J. Biol. Chem. 277, 16351-16354 (2002)) in 20 mM imidazole (pH 6.5), 100 mM KCl, 6 mM CaCl2 and 0.02% (w/v) NaN3. NMR samples were slightly under-titrated with peptide to ensure that all peptide was bound.

NMR Spectroscopy $O^2_{axis}$ parameters were determined from $T_1$ and $T_{1p}$ deuterium relaxation (Muhandiram, D. R. et al. *Measurement of H-2 T-1 and T-1p relaxation-times in uniformly C-13-Labeled and fractionally H-2-labeled proteins in solution. J. Am. Chem. Soc.* 117, 11536-11544 (1995)) measured at two magnetic fields. Rotational correlation times and $O^2_{NH}$ were determined from $^{15}N$ relaxation (Farrow, N. A. et al. *Backbone dynamics of a free and a phosphopeptide-complexed Src homology-2 domain studied by $^{15}N$ NMR relaxation. Biochemistry* 33, 5984-6003 (1994)) obtained at two magnetic fields. $O^2_{C\alpha CO}$ parameters were determined by transverse cross-correlated relaxation. Wang, T., Cai, S. & Zuiderweg, E. R. *Temperature dependence of anisotropic protein backbone dynamics. J. Am. Chem. Soc.* 125, 8639-8643 (2003). All measurements were made at 35° C. Model-free parameters (Lipari, G. & Szabo, A. *Model-free approach to the interpretation of nuclear magnetic-resonance relaxation in macromolecules.* 1. *Theory and range of validity. J. Am. Chem. Soc.* 104, 4546-4559 (1982)) were determined using a grid search approach (Dellwo, M J. & Wand, A. J. *Model-independent and model-dependent analysis of the global and internal dynamics of cyclosporine-A. J. Am. Chem. Soc.* 111, 4571-4578 (1989)) using a quadrupolar coupling constant of 167 kHz, an effective N—H bond length of 1.04 Å and $^{15}N$ tensor breadth of 170 p.p.m. The average error of $O^2_{axis}$, $O^2_{NH}$ and $O^2_{C\alpha CO}$ parameters across all complexes were estimated by Monte Carlo sampling to be 0.016, 0.011 and 0.024, respectively. The model-free parameters have been deposited in the Biological Magnetic Resonance Data Bank ("BioMagResBank," Eldon L. Ulrich; Hideo Akutsu; Jurgen F. Doreleijers; Yoko Harano; Yannis E. Ioannidis; Jundong Lin; Miron Livny; Steve Mading; Dimitri Maziuk; Zachary Miller; Eiichi Nakatani; Christopher F. Schulte; David E. Tolmie; R. Kent Wenger; Hongyang Yao; John L. Markley; *Nucleic Acids Research* 36, D402-D408 (2007) doi: 10.1093/nar/gkm957).

Data Interpretation

The change in conformational entropy of calmodulin on binding a target domain was estimated as the sum of three terms: $\Delta S_{conf}=\Delta S_{harm}+\Delta S_{rotamer(fast)}+\Delta S_{rotamer(slow)}$. $S_{harm}$ was obtained from $O^2_{axis}$ parameters using a harmonic oscillator model. Li, Z., Raychaudhuri, S. & Wand, A. J. *Insights into the local residual entropy of proteins provided by NMR relaxation. Prot. Sci.* 5, 2647-2650 (1996). Free calcium-saturated calmodulin was used as the reference state in site-to-site comparisons. To normalize the unequal number of resolved sites among the complexes, the average methyl order parameter within a complex was assigned to each unresolved site of that complex. A classical entropy term $\Delta S_{rotamer(fast)}$ was added to represent minor conformers that are sampled owing to fast rotameric interconversion. Lee, A. L. et al. *Temperature dependence of the internal dynamics of a calmodulin peptide complex. Biochemistry* 41, 13814-13825 (2002). For the small number of sites having multiple conformations in slow exchange on the NMR chemical shift timescale, an additional classical entropy contribution $\Delta S_{rotamer(slow)}$ was calculated on the basis of measured intensities. Populations of the three motional classes were obtained using nonlinear regression of a three gaussian model to the observed order parameter distributions.

The summed distribution of $O^2_{axis}$ axis parameters of all six complexes was fitted to a random distribution and to one, two- and three-gaussian distribution models. The bin size for this analysis was determined from a well-established formula for optimal bin width (Scott, D. *On optimal and data-based histograms. Biometrika* 10, 605-610 (1979)) and was found to be 0.05. Only the three-gaussian model could satisfactorily describe the data (P<0.0001), that is:

$$\text{Occurences}(O^2_{axis})=A_J\exp[((-O^2_{axis}-C_J)/W_J)^2/2]+A_\alpha\exp[((-O^2_{axis}-C_\alpha)/W_\alpha)^2/2]+A_\omega\exp[((-O^2_{axis}-C_\omega)W_\omega)^2/2] \quad (3)$$

where $A_i$, $C_i$ and $W_i$ define the population, centre and breadth, respectively, of the J, α and ω classes of motion.

The nine parameters were fitted using the nonlinear regression routine of SigmaPlot 2000 (SPSS). The summed distribution yielded fitted 3-gaussian distributions centred on $O^2_{axis}$ values of 0.35 (J-class), 0.58 (α-class) and 0.78 (ω-class). These centres were fixed in subsequent fitting of the $O^2_{axis}$ distributions of the individual complexes, from which the relative populations of each motional class were obtained. Uncertainties in the fitted populations were estimated by varying the $O^2_{axis}$ parameters by two standard deviations. This results in asymmetric error bars. The total change in conformational entropy of calmodulin on binding a target domain was calculated as the sum of three terms: $\Delta S_{conf}=\Delta S_{harm}+\Delta S_{rotamer(fast)}+\Delta S_{rotamer(slow)}$. Changes in conformational entropy $\Delta S_{rotamer(fast)}$ expressed as changes in motion within a rotameric well on the fast timescale (sub-ns) were obtained from the experimentally determined $O^2_{axis}$ parameters using a simple harmonic oscillator model. Li Z et al. (1996). To calculate changes in entropy derived from motion of the same oscillator, site-to-site comparison to free calcium-saturated calmodulin was used to provide a reference state. The change in the entropy reflected by the change in the motion of each methyl symmetry axis was estimated using $\Delta S_{harm}=-18\times\Delta O^2_{axis}$ J $mol^{-1}$ $K^{-1}$. See Li Z et al. (1996) for further details of the model. To normalize the unequal number of resolved sites among the complexes, the average methyl order parameter within a complex was assigned to each unresolved site of that complex. A classical entropy term ($\Delta S_{rotamer(fast)}$) was added to represent minor conformers that are sampled owing to fast rotameric interconversion that also contributes to the generalized order parameter. Lee, A. L. et al. *Temperature dependence of the internal dynamics of a calmodulin peptide complex. Biochemistry* 41, 13814-13825 (2002). For the small number of methyl sites having multiple conformations in slow exchange on the NMR chemical shift timescale, an additional classical entropy contribution ($\Delta S_{rotamer(slow)}$) was calculated using the measured intensities to provide populations.

Additional details regarding the present invention may be obtained from Frederick, K K et al., *Nature* 448, 325-329 (19 Jul. 2007)|doi:10.1038/nature05959 which is herein incorporated in its entirety.

What is claimed:

1. A method for the determination of the degree of molecular recognition of a protein for a ligand comprising:

determining the squared generalized order parameter ($O^2$) for at least one intramolecular bond of the protein;

forming a complex between the protein and the ligand;

determining $O^2$ for the said at least one bond of the protein while the protein and ligand are in a complex; and relating the $O^2$ value or values determined for the protein while the protein and ligand are in a complex to the $O^2$ value or values determined for the uncomplexed protein.

2. The method of claim 1 wherein said determinations are achieved through application of NMR spectroscopy.

3. The method of claim 1 wherein determining comprises treating of said bonds as simple harmonic oscillators.

4. The method according to claim 1 wherein said intramolecular bond comprises a bond in a methyl group.

5. The method according to claim 1 wherein said $O^2$ value is determined only for intramolecular bonds in methyl groups.

6. The method of claim 1 wherein relating includes evaluation of the conformational entropy of the protein and the complex of the protein and the ligand.

7. The method of claim 1 wherein said conformational entropy is empirically calibrated.

8. The method of claim 1 further comprising:

forming a complex between the protein and at least one further ligand;

determining $O^2$ for the said at least one bond of the protein while the protein and further ligands are in a complex; and relating the $O^2$ value or values determined for the protein while the protein and further ligand are in a complex to the $O^2$ value or values determined for the uncomplexed protein.

9. The method of claim 8 wherein said determinations are achieved through application of NMR spectroscopy.

10. The method of claim 8 wherein relating includes evaluation of the conformational entropy of the protein and the complexes of the protein with at least some of the ligand and further ligands.

11. The method of claim 8 wherein said conformational entropy is empirically calibrated.

12. The method of claim 8 wherein a plurality of further ligands are evaluated in complex with the protein.

13. The method of claim 8 performed iteratively with a plurality of further ligands.

14. The method of claim 1 wherein the conformational entropy of the protein and of the protein in complex with the ligand is ascertained.

15. The method of claim 8 further comprising identifying which of said ligand and further ligands has a relatively high degree of molecular recognition as compared with the average value of molecular recognition for the ligand and further ligands evaluated.

16. The method of claim 15 further comprising selecting at least one of said ligands identified as having a relatively high degree of molecular recognition as a lead drug candidate.

* * * * *

UNITED STATES PATENT AND TRADEMARK OFFICE

CERTIFICATE OF CORRECTION

PATENT NO. : 8,652,790 B2
APPLICATION NO. : 12/669626
DATED : February 18, 2014
INVENTOR(S) : Valentine et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 778 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 23
<212> TYPE: PRT
<213> ORGANISM: Homo sapiens

<400> SEQUENCE: 1

Lys Arg Arg Ala Ile Gly Phe Lys Lys Leu Ala Glu Ala Val Lys Phe
1               5                   10                  15

Ser Ala Lys Leu Met Gly Gln
            20


<210> SEQ ID NO 2
<211> LENGTH: 20
<212> TYPE: PRT
<213> ORGANISM: Homo sapiens
```

<400> SEQUENCE: 2

Arg Lys Lys Thr Phe Lys Glu Val Ala Asn Ala Val Lys Ile Ser Ala
1 5 10 15

Ser Leu Met Gly
20

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Gln Thr Glu Lys Met Trp Gln Arg Leu Lys Gly Ile Leu Arg Ser Leu
1 5 10 15

Val Lys Gln

<210> SEQ ID NO 4
<211> LENGTH: 22
<212> TYPE: PRT
<213> ORGANISM: Homo sapiens

<400> SEQUENCE: 4

Ala Lys Ser Lys Trp Lys Gln Ala Phe Asn Ala Thr Ala Val Val Arg
1 5 10 15

His Met Arg Lys Leu Gln
20

<210> SEQ ID NO 5
<211> LENGTH: 20
<212> TYPE: PRT
<213> ORGANISM: Gallus gallus

<400> SEQUENCE: 5

Ala Arg Arg Lys Trp Gln Lys Thr Gly His Ala Val Arg Ala Ile Gly
1 5 10 15

Arg Leu Ser Ser
20

<210> SEQ ID NO 6
<211> LENGTH: 24
<212> TYPE: PRT
<213> ORGANISM: Rattus norvegicus

<400> SEQUENCE: 6

Leu Ile Pro Ser Trp Thr Thr Val Ile Leu Val Lys Ser Met Leu Arg
1 5 10 15

Lys Arg Ser Phe Gly Asn Pro Phe
20

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 7

His His His His His His
1 5

-continued

```
<210> SEQ ID NO 8
<211> LENGTH: 51
<212> TYPE: PRT
<213> ORGANISM: Homo sapiens

<400> SEQUENCE: 8

Met Gly Ser Ser Ala Thr Glu Ile Glu Glu Leu Glu Asn Thr Thr Phe
1               5                   10                  15

Lys Tyr Leu Thr Gly Glu Gln Thr Glu Lys Met Trp Gln Arg Leu Lys
            20                  25                  30

Gly Ile Leu Arg Cys Leu Val Lys Gln Leu Glu Arg Gly Asp Val Asn
        35                  40                  45

Val Val Asp
    50
```